(12) United States Patent
Samukawa et al.

(10) Patent No.: US 9,620,338 B2
(45) Date of Patent: Apr. 11, 2017

(54) SYSTEM, METHOD, AND PROGRAM FOR PREDICTING PROCESSING SHAPE BY PLASMA PROCESS

(75) Inventors: Seiji Samukawa, Miyagi (JP); Kohei Ono, Tokyo (JP); Takuya Iwasaki, Tokyo (JP)

(73) Assignees: MIZUHO INFORMATION & RESEARCH INSTITUTE, INC., TOkyo (JP); TOHOKU TECHNOARCH CO., LTD., Sendai-shi, Miyagi (JP)

( * ) Notice: Subject to any disclaimer, the term of this patent is extended or adjusted under 35 U.S.C. 154(b) by 1012 days.

(21) Appl. No.: 13/635,600

(22) PCT Filed: Mar. 11, 2011

(86) PCT No.: PCT/JP2011/055848
§ 371 (c)(1),
(2), (4) Date: Sep. 17, 2012

(87) PCT Pub. No.: WO2011/115023
PCT Pub. Date: Sep. 22, 2011

(65) Prior Publication Data
US 2013/0013253 A1     Jan. 10, 2013

(30) Foreign Application Priority Data
Mar. 16, 2010  (JP) .................................. 2010-060028

(51) Int. Cl.
*G06F 15/00*     (2006.01)
*G01B 15/04*     (2006.01)
(Continued)

(52) U.S. Cl.
CPC ........ *H01J 37/32954* (2013.01); *G01N 21/67* (2013.01); *H01L 21/31116* (2013.01); *H01L 22/26* (2013.01); *H01L 2924/0002* (2013.01)

(58) Field of Classification Search
CPC ...... G01B 11/24; G01B 21/20; G01M 11/025; G06K 9/6247; G01K 13/002; G01N 21/718; G01N 21/75
(Continued)

(56) References Cited

U.S. PATENT DOCUMENTS 4,344,142 A * 8/1982 Diehr, II ............. B29C 35/0288
                                                    264/325
5,070,469 A * 12/1991 Kunikiyo et al. ................ 703/2
(Continued)

FOREIGN PATENT DOCUMENTS

JP          9-266199 A     10/1997
JP          9-313925 A     12/1997
(Continued)

OTHER PUBLICATIONS

Benjamin Martin, STIC, Mar. 23, 2015, STIC.*
(Continued)

*Primary Examiner* — John Breene
*Assistant Examiner* — Mohammad Islam
(74) *Attorney, Agent, or Firm* — Westerman, Hattori, Daniels & Adrian, LLP

(57) ABSTRACT

A system, a method, and a program for predicting a processing shape formed by a plasma process, including databases for apparatus condition, incident ion, incident radical, actual measurement, material property and surface reaction, as well as a trajectory calculation unit, and a surface shape calculation unit. The trajectory calculation unit calculates the trajectories of the respective ions incident on the surface of the substrate based on information and data obtained from the databases and from measurement data from an on-wafer monitoring sensor. Based on the calculation result by the trajectory calculation unit, the surface shape calculation unit
(Continued)

calculates the change of the shape by referring to the data stored in the material property and surface reaction DB.

7 Claims, 20 Drawing Sheets

(51) Int. Cl.
*H01J 37/32* (2006.01)
*G01N 21/67* (2006.01)
*H01L 21/311* (2006.01)
*H01L 21/66* (2006.01)

(58) Field of Classification Search
USPC .......................................... 702/167, 155, 85
See application file for complete search history.

(56) References Cited

U.S. PATENT DOCUMENTS

| | | | | |
|---|---|---|---|---|
| 5,421,934 A | * | 6/1995 | Misaka | H01L 21/30 216/59 |
| 5,728,253 A | * | 3/1998 | Saito | B81C 1/00587 118/712 |
| 5,733,820 A | * | 3/1998 | Adachi | G01N 21/68 216/59 |
| 6,153,115 A | * | 11/2000 | Le | H01J 37/32935 216/60 |
| 6,355,570 B1 | * | 3/2002 | Nakata | G01N 21/53 438/706 |
| 6,577,915 B1 | * | 6/2003 | Cooperberg | H01J 37/32935 438/9 |
| 8,209,155 B2 | * | 6/2012 | Ichikawa | G06F 17/5018 703/2 |
| 8,545,669 B2 | * | 10/2013 | Mahoney | H01J 37/32935 156/345.24 |
| 2001/0014520 A1 | * | 8/2001 | Usui | C23C 16/50 438/586 |
| 2002/0123229 A1 | * | 9/2002 | Ono | H01L 21/32136 438/706 |
| 2002/0195423 A1 | * | 12/2002 | Patel | B81C 1/00476 216/73 |
| 2004/0007326 A1 | * | 1/2004 | Roche | H01J 37/32935 156/345.24 |
| 2004/0115872 A1 | * | 6/2004 | Koulik | H05H 1/48 438/200 |
| 2005/0009347 A1 | * | 1/2005 | Matsumoto | G01N 21/68 438/689 |
| 2005/0011611 A1 | * | 1/2005 | Mahoney | H01J 37/32935 156/345.24 |
| 2005/0016953 A1 | * | 1/2005 | Arai | G01N 15/0205 216/59 |
| 2005/0028049 A1 | * | 2/2005 | Poolla | H01L 21/67253 714/699 |
| 2005/0151544 A1 | * | 7/2005 | Mahoney et al. | 324/655 |
| 2005/0278057 A1 | * | 12/2005 | Cooperberg et al. | 700/121 |
| 2006/0043064 A1 | * | 3/2006 | Tanaka | G01N 21/68 216/61 |
| 2007/0197041 A1 | * | 8/2007 | Nakaya | H01J 37/3266 438/717 |
| 2007/0201016 A1 | * | 8/2007 | Song | G01N 21/68 356/72 |
| 2009/0253222 A1 | * | 10/2009 | Morisawa | G01B 11/0658 438/9 |
| 2010/0072391 A1 | * | 3/2010 | Hopwood | G01N 15/0656 250/397 |
| 2010/0243431 A1 | * | 9/2010 | Kuboi et al. | 204/192.33 |
| 2010/0255683 A1 | * | 10/2010 | Godet et al. | 438/710 |
| 2011/0315661 A1 | * | 12/2011 | Morisawa | G01N 21/68 216/60 |
| 2012/0029836 A1 | * | 2/2012 | Hermann | G01J 3/443 702/28 |
| 2012/0074514 A1 | * | 3/2012 | Nguyen | H01L 21/67253 257/467 |
| 2012/0175515 A1 | * | 7/2012 | Hori | G01N 27/622 250/282 |
| 2012/0177537 A1 | * | 7/2012 | Aota | G01N 1/4005 422/69 |

FOREIGN PATENT DOCUMENTS

| | | |
|---|---|---|
| JP | 2000-150607 A | 5/2000 |
| JP | 2003-282546 A | 10/2003 |
| JP | 2004-266098 A | 9/2004 |
| JP | 2005-217276 A | 8/2005 |
| JP | 2005-277361 A | 10/2005 |
| JP | 2009-283838 A | 12/2009 |

OTHER PUBLICATIONS

Supreme Court, Alice Corp. Vs CLS et al., Oct. 2013, pp. 1-23.*
International Search Report of PCT/JP2011/055848; mailing date Jun. 28, 2011.
Misaka, et al., "Novel Surface Reaction Model in Dry-Etching Process Simulator", Japanese Journal of Applied Physics, Dec. 1992, vol. 31, Part I, No. 12B, (pp. 4363-4369).
Seiji Onoue, "TCAD Simulation for Virtual Design of Semiconductor Processes", Toshiba Review, vol. 58, No. 6, pp. 60-63, Toshiba Corporation, Japan, Jun. 1, 2003, cited in Japanese Office Action dated Jan. 27, 2015 with English concise explanation (7 pages).
Hideki Fujita, "Recent CAE Technology in Nissin Electric", The Nissin Electric Review, vol. 48, No. 1 p. 6, Nissin Electric Co., Ltd., Japan, Mar. 20, 2003, cited in Japanese Office Action dated Jan. 27, 2015 with English concise explanation (4 pages).
Japanese Office Action dated Jan. 27, 2015, issued in corresponding JP Patent Application No. 2012-505650 (3 pages).

* cited by examiner

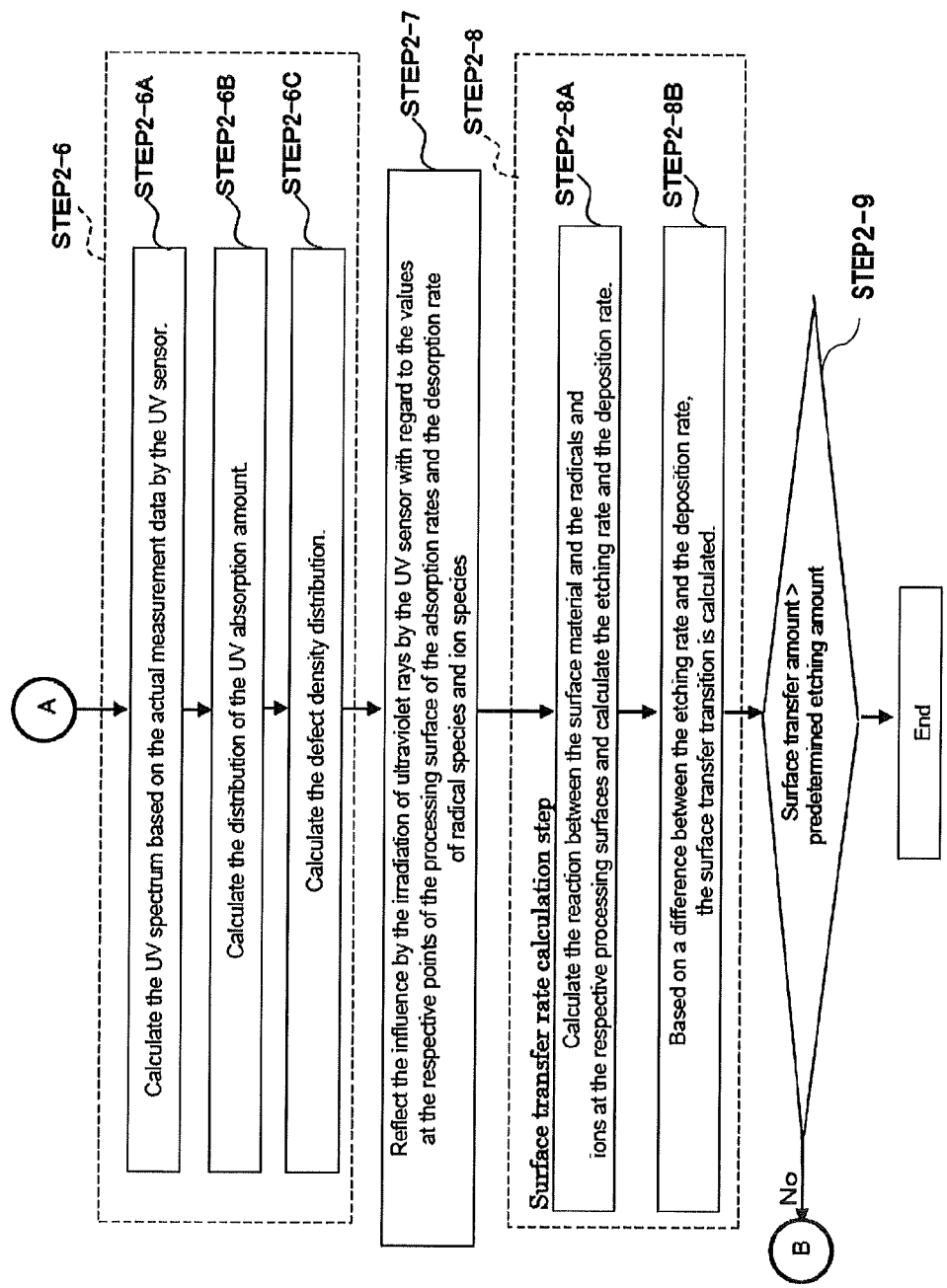

SYSTEM, METHOD, AND PROGRAM FOR PREDICTING PROCESSING SHAPE BY PLASMA PROCESS

TECHNICAL FIELD

The present invention relates to a system, a method, and a program for predicting, based on actual plasma measurement data, a processing shape by a plasma process.

BACKGROUND ART

In a semiconductor manufacture process, an increase of the number of steps requires a manufacture process to be performed stably and accurately. With regard to this point, Patent Literature 1 discloses the following matter. Specifically, in a process apparatus for sequentially performing a plurality of steps on a to-be-machined object, the processing state or the state of the process apparatus in a predetermined step among the respective processings is monitored. Depending on the monitoring result, the shape of the to-be-machined object in the predetermined step is simulated. A dislocation between this simulated shape and a standard shape determined in advance is detected and processing conditions are set to compensate the detected dislocation in a step subsequent to the predetermined step.

Although not specifically disclosed in Patent Literature 1, a method by plasma simulation has been conventionally used as a method of calculating a shape by plasma etching or plasma deposition. According to this method, based on external plasma parameters (e.g., a power supply voltage, a pressure, or gaseous species for generating plasma), plasma electrons or an ion density or temperature is firstly calculated to thereby calculate the type, density, or energy of the ions or radicals flowing in the substrate for example. Thereafter, a reaction coefficient is given artificially to calculate the etching shape in a time-series manner.

On the other hand, the process is optimized by calculating the electron temperature, the electron density, or the active species of the plasma for example in the semiconductor manufacture process. Patent Literature 2 discloses an on-wafer monitoring sensor to measure the plasma on a wafer surface. This on-wafer monitoring sensor includes a plurality of detection functions by which the energy distribution of incident ions to the substrate surface can be measured, VUV (vacuum ultra-violet rays) photons can be detected, the charge accumulation amount can be measured, and any or both of the combination of the electron temperature and the electron density and the combination of the ion current and the sheath voltage can be measured. This on-wafer monitoring sensor can be combined with other detection method (e.g. emission spectrometry) to thereby measure radical species or ion species.

CITATION LIST

Patent Literature

Patent Literature 1: JP 2005-277361A
Patent Literature 2: JP 2003-282546A

Non-Patent Literature

Non-Patent Literature 1: A. MISAKA, K. HARAFUJI, M. KUBOTA AND N. NOMURA, "Novel Surface Reaction Model in Dry-Etching Process Simulator", JPN. J. APPL. PHYS 31 PAGE. 4363-4669 (1992)

SUMMARY OF INVENTION

Technical Problem

Even when the to-be-etched shape is calculated by the plasma simulation as described above, the calculated ion trajectory and the etching shape correspond, in reality, to the actual ion trajectory and etching shape only under limited conditions. Thus, as disclosed in Patent Literature 1, no processing conditions are found in order to compensate the dislocation.

Furthermore, even when the same external plasma parameters are used, a significant difference is caused in the plasma state depending on apparatus configurations in reality.

In view of the above, it is an objective of the present invention to provide a system, a method, and a program for predicting the shape by a plasma process by which various sensors can be used to measure the process state on a realtime basis to predict the shape based on the plasma measurement data.

Solution to Problem

In order to achieve the above objective, a system for predicting a processing shape by a plasma process to predict a processing surface shape formed by a plasma processing apparatus based on actual measurement data from a sensor for monitoring a plasma state, the sensor being stored in the plasma processing apparatus together with a processing object, includes:

an incident ion database for storing, with regard to the respective operating conditions of the plasma processing apparatus, data regarding an incident energy distribution and an angle distribution of the flux of charged particles;

an incident radical database for storing, with regard to the respective operating conditions of the plasma processing apparatus, data regarding an incident energy distribution and an incident angle distribution of radicals;

a material property and surface reaction database for storing the respective coefficients for the respective reactions required for a radical adsorption reaction calculation, an ion reaction calculation and a thermal excitation-type chemical reaction calculation, respectively, and the property values of the respective materials required for a trajectory calculation and a reaction calculation;

an actual measurement database for storing, with regard to the respective operating conditions of the plasma processing apparatus, an electron temperature and an electron density from actual measurement data from the sensor so that the electron temperature and the electron density are associated with the data stored in the incident ion database and the incident radical database, respectively;

a trajectory calculation unit for calculating the trajectories of charged particles incident on the processing surface from plasma based on an electron temperature, an electron density, and an electron energy distribution calculated from a current-voltage characteristic from among the actual measurement data inputted from the sensor as well as a charge distribution at the processing surface or based on an ion current and sheath voltage calculated from the current-voltage characteristic and the charge distribution at the processing surface; and a surface shape calculation unit for calculating the respective ions incident on the respective points of the processing surface based on the trajectories of the charged particles calculated by the trajectory calculation unit to use the data stored in the incident ion database, the incident radical database, the material property and surface reaction database, and the actual measurement database, for calculating the reactions at the respective points of the processing surface to calculate an etching rate and a deposition rate, and for calculating, based on a difference between the etching rate and the deposition rate, the transfer rates at the respective points of the processing surface to thereby calculate the surface shape.

A method of predicting a processing shape by a plasma process, wherein the neighborhood of a substrate surface is divided to a plurality of elements, an initial state and a plasma processing condition are set, and a processing surface shape caused by a plasma process is predicted, includes:

a trajectory calculation step for calculating, based on an electron temperature, an electron density, and an electron energy distribution calculated from a current-voltage characteristic from among actual measurement data for plasma generated under a processing condition and a charge distribution at the processing surface or based on an ion current and a sheath voltage calculated from the current-voltage characteristic and the charge distribution at the processing surface, the trajectories of charged particles flowing from plasma into the processing surface;

a surface transfer rate calculation step for calculating ion species incident on the respective points of the processing surface along the trajectories of the charged particles calculated in the trajectory calculation step and using an incident flux distribution of the ion species and radicals, for calculating an etching rate and a deposition rate at the respective points of the processing surface and for calculating, based on a difference between the etching rate and the deposition rate, the transfer rates at the respective points of the surface; and a step for determining, based on the transfer rates at the respective points of the processing surface calculated in the surface transfer rate calculation step, whether a processing amount set by the processing condition is satisfied or not to newly set, when the processing amount set by the processing condition is not satisfied, new points at the processing surface to return to the trajectory calculation step.

A program of predicting a processing shape by a plasma process, wherein the neighborhood of a substrate surface is divided to a plurality of elements, an initial state and a plasma processing condition are set, and a processing surface shape caused by a plasma process is predicted, includes:

a trajectory calculation step for calculating, based on an electron temperature, an electron density, and an electron energy distribution calculated from a current-voltage characteristic from among actual measurement data for plasma generated under a processing condition and a charge distribution at the processing surface or based on an ion current and a sheath voltage calculated from the current-voltage characteristic and the charge distribution at the processing surface, the trajectories of charged particles flowing from plasma into the processing surface;

a surface transfer rate calculation step for calculating ion species incident on the respective points of the processing surface along the trajectories of the charged particles calculated in the trajectory calculation step and using an incident flux distribution of the ion species and radicals, for calculating an etching rate and a deposition rate at the respective points of the processing surface and for calculating, based on a difference between the etching rate and the deposition rate, the transfer rates at the respective points of the surface; and a step for determining, based on the transfer rates at the respective points of the processing surface calculated in the surface transfer rate calculation step, whether a processing amount set by the processing condition is satisfied or not to newly set, when the processing amount set by the processing condition is not satisfied, new points at the processing surface to return to the trajectory calculation step.

Advantageous Effects of Invention

According to the present invention, sensors can be used to measure the plasma state on a realtime basis to predict the processing shape based on the measurement data. Thus, when the predicted processing shape is not a predetermined shape, the plasma processing apparatus conditions can be changed to obtain the predetermined processing shape.

BRIEF DESCRIPTION OF THE DRAWINGS

FIG. 7B is a view showing the remaining part of the flow shown in FIG. 7A.

DESCRIPTION OF EMBODIMENTS

The following section will describe in detail some embodiments of the present invention with reference to the drawings.

[System for Predicting Processing Shape by Plasma Process]

Figure 1:
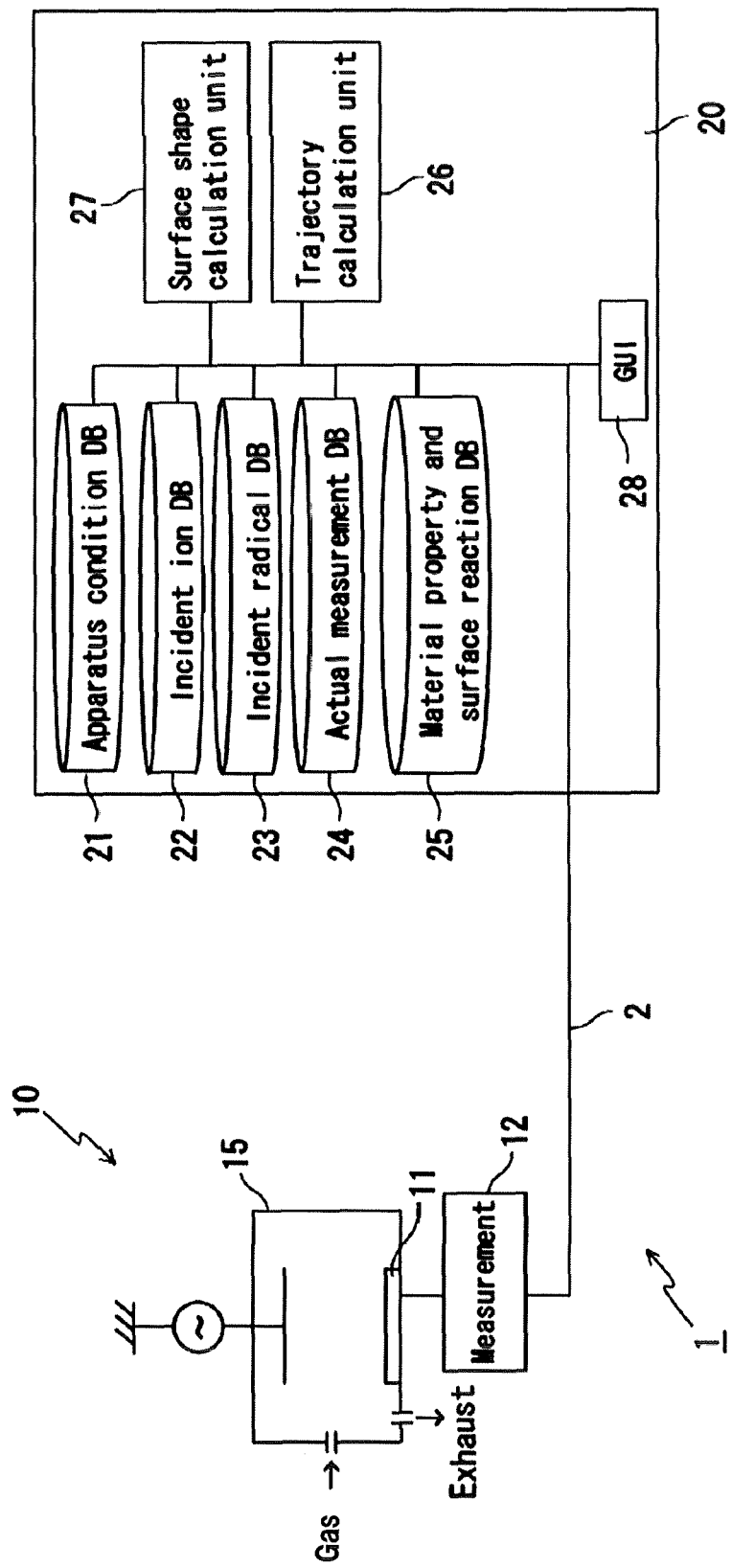
FIG. 1 is a block diagram of a system for predicting processing shape by plasma process according to the present invention.

FIG. 1 illustrates the configuration of a system for predicting the processing shape by plasma process according to an embodiment of the present invention. A prediction system 1 according to an embodiment of the present invention is configured so that a plasma processing apparatus 10 and a simulator 20 are connected by a network 2 for example. The network 2 is not limited to the configuration as shown in FIG. 1 in which the network 2 is configured by a wire. The network 2 also can be configured to be wirelessly connected to an wireless communication section included in an on-wafer monitoring sensor 11 in the plasma processing apparatus 10, configured by a wire via a port in a chamber 15 or configured by the combination thereof.

The plasma processing apparatus 10 functions, for example, to introduce gas into the chamber 15 to discharge the gas by high-frequency or microwave power to thereby subject a substrate (not shown) stored in the chamber 15 to a processing treatment. The processing treatment includes an etching processing and a film formation processing. The chamber 15 also stores, in addition to the substrate, the on-wafer monitoring sensor 11 functioning as a sensor to monitor the plasma state and the substrate state. The on-wafer monitoring sensor 11 is connected, for example, to a measurement 12. Thus, the current flowing when a voltage is applied to a predetermined electrode in the on-wafer monitoring sensor 11 can be measured or the current caused by photons can be measured. The measurement 12 may be provided, as shown in FIG. 1, at the outer side of the chamber 15 or also may be provided in the on-wafer monitoring sensor 11 itself. The details of the on-wafer monitoring sensor 11 will be described later.

The simulator 20 includes: an apparatus condition database (Data Base, which will be abbreviated as DB) 21; an incident ion DB 22; an incident radical DB 23; an actual measurement DB 24; a material property and surface reaction DB 25; a trajectory calculation unit 26; a surface shape calculation unit 27; and a GUI (Graphical User Interface) 28 for providing a convenient operation. This simulator 20 may be configured so that a computer stores therein a program for predicting the processing shape by a plasma process according to the embodiment of the present invention and the program may be executed by the computer. Thus, the program for predicting the processing shape by a plasma process may be stored in a computer-readable recording medium. The term "program" herein means instructions to a computer combined to provide one result.

The apparatus condition DB 21 is a database to store the information related to the apparatus condition (e.g., the type, model number, or processing conditions of the plasma processing apparatus). The apparatus condition DB 21 stores therein, with regard to the respective plasma processing apparatuses, apparatus operating conditions (e.g., the gaseous species, the gas flow rate, the gas pressure, the input power) and data such as the substrate type or material.

The incident ion DB 22 is a database that stores therein, with regard to the respective operating condition of the plasma processing apparatuses, the data regarding the flux of charged particles. Data items stored in this incident ion DB 22 include ion species, incident energy distribution, and incident angle distribution. The incident ion DB 22 stores therein, with regard to the respective types and operating conditions of the plasma processing apparatus 10, the data regarding various ions such as $Cl_2^+$ or $SF_5^+$ and the incident energy distribution and the angle distribution of the electron charged particles flux for example. These values are calculated by the trajectory calculation unit 26 based on the measurement data from a sensor for sheath monitoring or a charge-up sensor in the on-wafer monitoring sensor 11.

The incident radical DB 23 is a database that stores therein, with regard to the respective operating conditions of the plasma processing apparatus, data regarding the radical flux. Data items stored in the incident radical DB 23 include radical species, incident energy distribution, and incident angle distribution. The incident radical DB 23 stores therein, with regard to the respective types, model number, and operating conditions of the plasma processing apparatus 10, data regarding various radical flux incident energy distributions and angle distributions (e.g., $CF_3^*$, $F^*$, $O^*$) for example. These values are based on the measurement result obtained by another method without using the on-wafer monitoring sensor 11.

The actual measurement DB 24 is a database that stores therein, with regard to the respective operating conditions of the plasma processing apparatus 10, the electron temperature and the electron density calculated based on the actual measurement data outputted from the on-wafer monitoring sensor 11 and/or that stores therein the ion current and the sheath voltage. The actual measurement DB 24 stores therein data regarding the sheath shape while being associated with the data stored in the incident ion DB 22 and the incident radical DB 23, respectively. Specifically, the actual measurement DB 24 stores therein the data calculated based on the actual measurement data by the on-wafer monitoring sensor 11 with regard to the process characteristic data caused by ions and photons incident on the object processed by the plasma processing apparatus 10 (e.g., the defect generation rate, the charge accumulation rate, or the processing shape). Stored data items include an ultra-violet radiation spectrum, a substrate potential, a lower electrode potential, an electron temperature, an electron density, an ion current, and a sheath voltage for example. The data stored in the actual measurement DB 24 is correlated to the data stored in the incident ion DB 22 and the incident radical DB 23 by the multivariate analysis technique such as a neural network. The configuration as described allows, when the actual measurement DB 24 receives the actual measurement data from the on-wafer monitoring sensor 11, the trajectory calculation unit 26 and the surface shape calculation unit 27 to predict the defect distribution or the processing shape for example.

The material property and surface reaction DB 25 stores therein the data required for the trajectory calculation by the trajectory calculation unit 26 and the data required for the reaction calculation by the surface shape calculation unit 27. The data stored in the material property and surface reaction DB 25 includes data regarding a material property and data regarding a surface reaction. For example, the trajectory calculation unit 26 performs analysis using a Poisson equation or a Newton's equation of motion and thus stores therein data regarding the permittivities or conductivities of the respective materials and the ion species and the electron mass for example. The surface shape calculation unit 27 performs a radical adsorption reaction calculation, an ion reaction calculation, and a thermal excitation-type chemical reaction calculation. Thus, the surface shape calculation unit 27 stores therein the respective coefficients for the respective reactions required in the respective calculations. Data items stored for the surface shape calculation unit 27 include: the rate of the defect generation due to ultra-violet rays; the adsorption rate of incident radicals and ions; the reaction probability; the reaction product type; and the angle distribution or the energy distribution when the reaction product is discharged again from the surface. Regarding such data stored in the material property and surface reaction DB 25 that is difficult to obtain through an experiment, the calculation result obtained by the quantum-mechanical calculation method (e.g., the first principle calculation, the molecular dynamics calculation) may be stored.

The material property data includes, in addition to the combination of the name of a reaction product at a substrate surface and any of etching or deposition, the particle number density (e.g., the atom number density or the molecule number density), the surface density of the adsorption site, the relative permittivity, the annihilation factor, the conductivity of conductive material, the electrical property (e.g., whether conductive or insulating), the light absorption coefficient of each wavelength, and the defect generation coefficient for each wavelength for example. The term "material" herein means such material that forms a reaction product and a substrate material. On the other hand, surface reaction data includes data regarding a neutral particle adsorption model, an ion reaction model, and a thermal excitation-type chemical reaction model, respectively. Data items regarding the neutral particle adsorption reaction model include: the name of a reactive product by the adsorption reaction; the adsorption rate of each incident radical and each reaction product; the angle dependence of the radical adsorption; and the radical reflectivity for example. Data items regarding the ion reaction model include: a combination of a substrate material or reaction product name having an ion assist reaction and an ion name; a desorption rate; and a reaction rate of an ion assist reaction for example. Data items regarding the thermal excitation-type chemical reaction model include a reaction coefficient of a thermal excitation-type chemical reaction and an activation energy for example.

The trajectory calculation unit 26 calculates the trajectory of charged particles required for the surface shape calculation unit 27. The trajectory calculation unit 26 calculates the trajectories of various ions or electrons incident on the substrate surface based on the data acquired from the apparatus condition DB 21 and the incident ion DB 22 depending on the processing conditions by the plasma processing apparatus 10, the data from the actual measurement DB 24 depending on the processing conditions by the plasma processing apparatus 10, and the actual measurement data from the on-wafer monitoring sensor 11.

The trajectory calculation unit 26 generally calculates the trajectories of the charged particles incident on the processing surface from plasma based on, from among the actual measurement data inputted from the on-wafer monitoring sensor 11 and other sensors, the electron temperature, the electron density and the energy distribution of electron calculated from the current-voltage characteristic and the charge distribution at the processing surface or based on the ion current and the sheath voltage calculated from the current-voltage characteristic and the charge distribution at the processing surface. For example, the trajectory calculation unit 26 also may be configured, instead of using the data stored in the apparatus condition DB 21, the incident ion DB 22, and the actual measurement DB 24, to calculate the sheath voltage based on the potential, the electron temperature, and the electron density at the processing surface calculated by the sensor for sheath monitoring in the on-wafer monitoring sensor 11 and an optional charge-up sensor to thereby calculate the charged particles flowing into the substrate (i.e., the respective trajectories of the electrons and ions). Specifically, the Poisson equation is solved based on the accumulated charge distribution at the processing surface to thereby calculate the electric field caused by the charge accumulation distribution. Thereafter, based on the electric field distribution, the trajectories of the charged particles flowing into the substrate surface are calculated.

Based on the calculated ion trajectories, the ion flux distribution is calculated as a function of the energy and angle. These values may be stored in the incident ion DB 22 and may be used for the calculation by the surface shape calculation unit 27.

The surface shape calculation unit 27 calculates a change in the shape by the plasma process. The surface shape calculation unit 27 calculates a change of the shape of the surface due to the radical adsorption reaction, the ion assist reaction, and the thermal excitation-type chemical reaction based on the calculation result by the trajectory calculation unit 26 while referring to the data stored in the material property and surface reaction DB 25.

The surface shape calculation unit 27 calculates, based on conditions (e.g., the respective flux densities of the radicals and ions flowing from plasma, the adsorption probability to the wafer surface, the chemical reaction rate, and the reflectivity), the etching rate and the deposition rate of each material at each point on the processing surface to calculate the transition of the transfer of the surface based on the difference between the etching rate and the deposition rate to thereby calculate, for example, a temporal change of the cross-sectional shape of the wafer.

The surface shape calculation unit 27 can calculate the surface shape in consideration of a defect occurrence caused by the radiation of ultra-violet rays as well as a change of the etching rate due to the defect.

The defect caused by ultra-violet rays can be calculated by a procedure as shown below. Specifically, based on the ultra-violet radiation spectrum measured by the UV sensor in the on-wafer monitoring sensor 11, the intensity of the ultra-violet rays entering the processing surface is calculated by angular integration. Then, based on the intensity values of the ultra-violet rays radiated to the respective points near the processing surface, an average defect number per a unit time is calculated. Then, this average defect number can be subjected to time integration to thereby calculate the defect density distribution.

Figure 2:
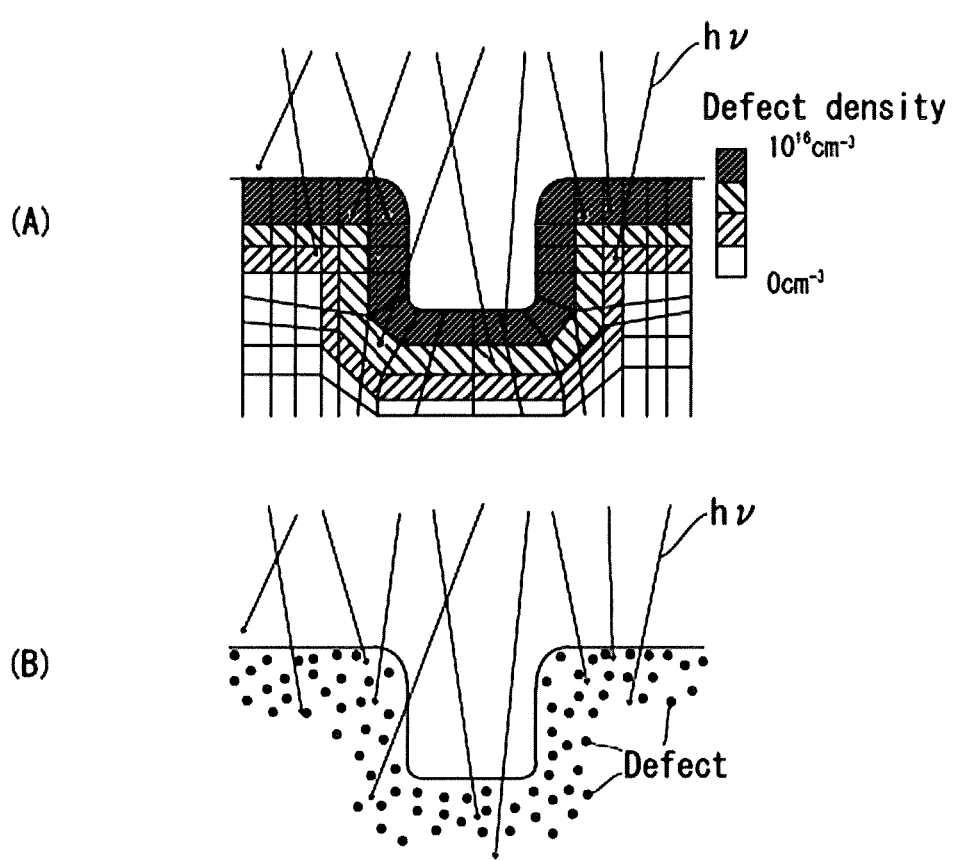
FIG. 2 (A) is a view schematically showing a defect caused by absorption of ultra-violet rays represented as a continuum model, and (B) is that represented as a particle model.

A defect can be represented by various methods, including the one using a continuum model and the one using a particle model. The magnitude of the defect density is a merkmal for using these methods. When a defect is represented as a continuum model, the defect distribution is handled as a continuum. As shown in FIG. 2(A), the material interior is divided in a grid-like manner. Then, the respective resultant grid points or cells are given with the defect density represented as a real number. When a defect is represented as a particle model, the one defect is represented as one particle. As shown in FIG. 2(B), the coordinate values of the respective defects are stored as data. A position at which the defect occurs is determined based on the intensity of ultraviolet rays and using a random number in consideration of the probability distribution. The reason is that there is a limitation in handling a defect as a continuum because only about a few dozens to a few hundreds of atoms exist within a line width of a few nanometers.

[Method of Predicting Processing Shape by Plasma Process]

The following section will describe the method of predicting the processing shape using the system 1 for predicting the processing shape by a plasma process according to an embodiment of the present invention.

[Assumption]

First, as an assumption for the explanation of how to predict the processing shape by a plasma process, how to describe the state of the processing surface and how to describe a change of the surface state will be explained conceptually.

Figure 3:
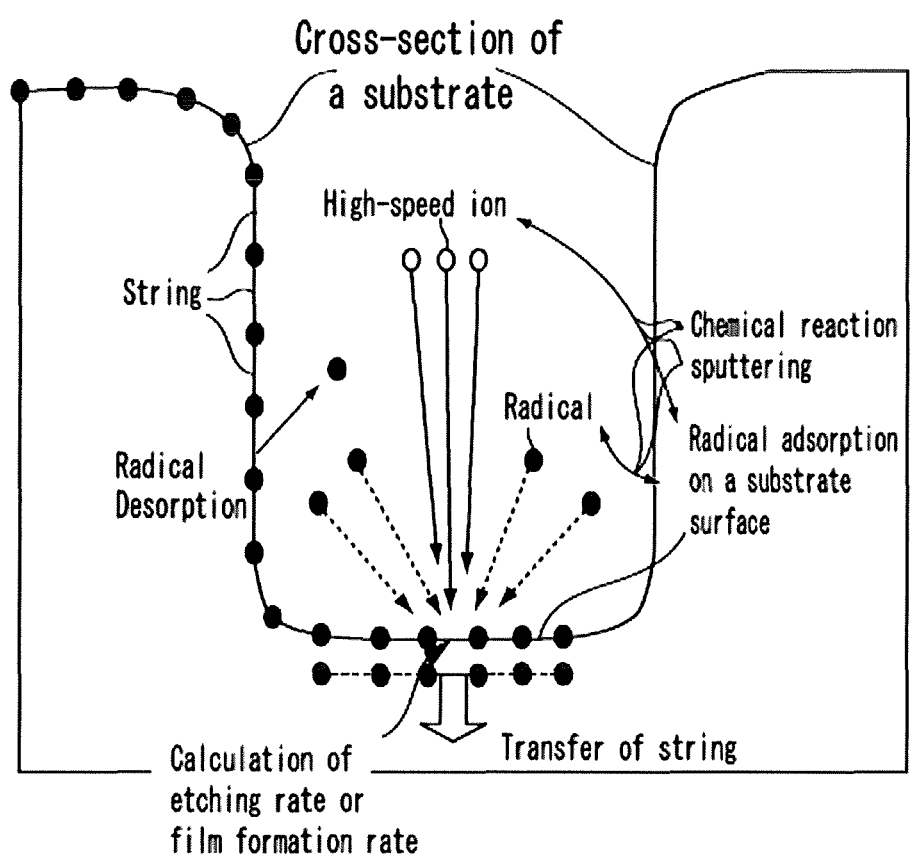
FIG. 3 is a view schematically showing a substrate surface processed by a plasma etching.

FIG. 3 is a schematic view illustrating a substrate surface processed by a plasma etching. When the substrate surface is subjected to ion etching at a high speed, the processing surface includes therein a chemical reaction and sputtering. Thus, the contour of the substrate surface is firstly represented by discrete black points (●) that are connected by straight lines. The straight lines are called strings. When radicals or high-speed ions are incident on the surface, the surface has a chemical reaction or sputtering and radicals are adsorbed or desorbed on the substrate surface. They are represented by a deposition rate and an etching rate. A difference between these rates is used to calculate the etching rate or film formation rate to transfer the strings. Although the following section will describe a two-dimensional shape, the description also can be applied to a three-dimensional shape.

Figure 4:
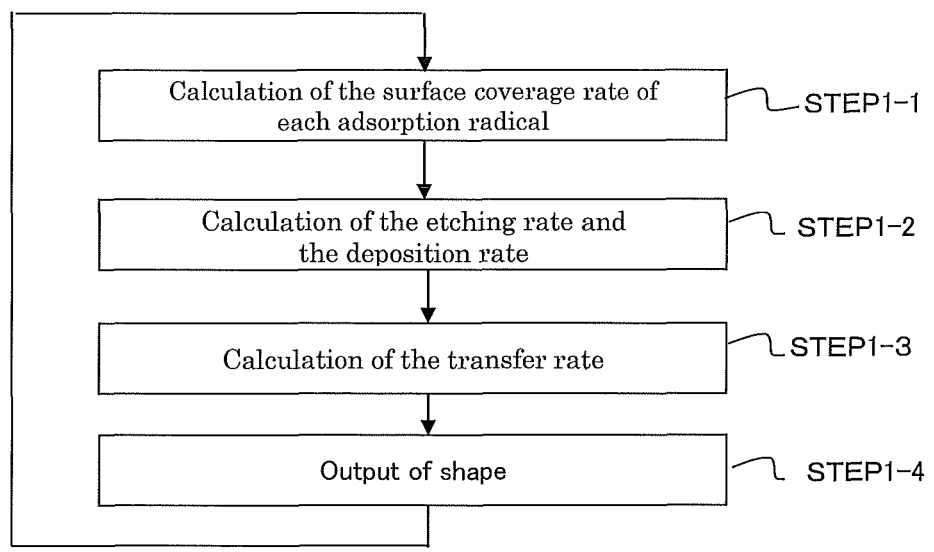
FIG. 4 is a view showing the outline of the general calculation flow of the processing surface shape.
Figure 5:
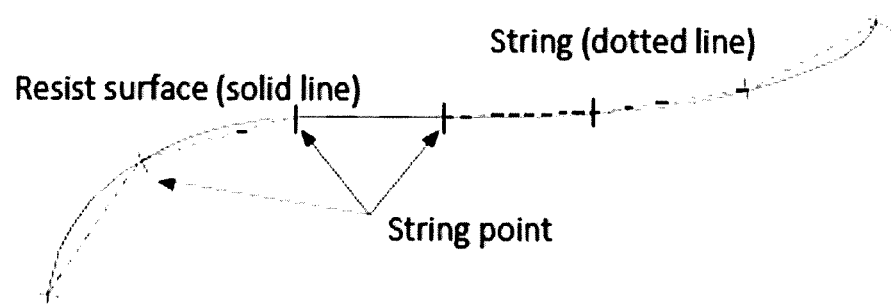
FIG. 5 is a view illustrating a method to describe a processing surface in a two-dimensional shape.

FIG. 4 illustrates the outline of the general calculation flow of the processing surface shape. As shown in FIG. 5, the resist surface shown by the solid line is divided by string points (generally, "the respective points on the processing surface") and the neighboring string points are approximated by strings as shown by the dotted line (generally "elements"). How to describe the surface reaction on this string will be considered. When it is assumed that the surface occupation rate of the substrate material is $\theta_0$, the surface occupation rate of the material m is $\theta_m$, and the surface density of the adsorption site is $\delta_s$, the following equation is established as a binding condition.

[Formula 1]

$$\theta_0(P, t) + \sum_{m=1}^{N} \theta_m(P, t) = 1 \tag{1}$$

[Formula 2]

$$\theta_m(P, t) \geq 0 \text{ for } m = 0, 1, \ldots, N \tag{2}$$

When assuming that the generation number of the material m per a unit time is $G_m$ and the disappearance number of the material m per a unit time is $H_m$, then the following basic equation is established.

[Formula 3]

$$\sigma_s \frac{d\theta_0}{dt}(P, t) = -\sum_{m=1}^{N} [G_m(P, t) - H_m(p, t)] \tag{3}$$

[Formula 4]

$$\sigma_m \frac{d\theta_m}{dt}(P, t) = G_m(P, t) - H_m(P, t) \tag{4}$$

Thus, by solving the basic equations based on the binding condition, the surface coverage rate of each adsorption radical is calculated (STEP1-1). The material m also may be called a radical.

Next, the etching rate and the deposition rate are calculated (STEP1-2). The etching rate is calculated as a sum of the etching rate by the thermal excitation-type chemical reaction, the etching rate by the physical sputtering, and the etching rate by the ion assist reaction. The deposition rate is calculated as a sum of the deposition rate caused by the accumulation effect of the deposition substance, the deposition rate by the generation of the deposition substance, and the deposition rate by the ion assist reaction. The etching rate and the deposition rate by plasma are calculated as shown by the following formula (Non-Patent Literature 1).

Specifically, the etching rate ER is decomposed as shown by the formula (5). $ER_{total}$ is the etching rate by the thermal excitation-type chemical reaction at the surface covered with the adsorption radical. $ER_{physical}$ is the etching rate by the physical sputtering to the clean surface of the to-be-etched material by high energy ions. $ER_{ionassisted}$ is the etching rate by the physical and chemical sputterings (also called "ion assist reaction") to the surface covered with the adsorption radical by high energy ions.

[Formula 5]

$$ER_{total} = ER_{thermal} + ER_{physical} + ER_{ionassisted} \tag{5}$$

The respective etching rates $ER_{thermal}$, $ER_{physical}$, and $ER_{ionassisted}$ can be calculated as shown below. The thermal excitation-type chemical reaction etching rate $ER_{thermal}$ at the point P is represented by the formula (6).

[Formula 6]

$$ER_{thermal}(P) = \frac{1}{\rho} \sum_n k_0^{(n)} \theta_n(P) \exp\left(-\frac{E_a^{(n)}}{k_B T}\right) \tag{6}$$

In the formula, $\rho$ is a substrate density, $k_0^{(n)}$ is the coefficient related to the radical n, $\theta_n$ is a surface occupation rate of the radical n, $E_a^{(n)}$ is an activation energy, $k_B$ is a Boltzmann constant, and T is a substrate temperature. As can be seen from the formula (6), $ER_{thermal}$ is a sum for the radical n.

The etching rate $ER_{physical}$ by the physical sputtering at the point P is represented by the formula (7).

[Formula 7]

$$ER_{physical}(P) = \frac{1}{\rho} \sum_i \int_0^{\varepsilon_{max}} Y_i^{physical}(\varepsilon) F_i(P, \varepsilon) \theta_0(P) d\varepsilon \tag{7}$$

In the formula, $\epsilon_{max}$ is the maximum energy of incident ion. $Y_i^{physical}(\epsilon)$ is the physical sputtering yield by the ion i. $F_i(P, \epsilon)$ is the flux of the incident ion i having the energy $\epsilon$ at the point P. $\theta_0(P)$ is a clean substrate surface occupation rate at the point P. As can be seen from the formula (7), $ER_{physical}$ is a sum for both ions i of the reactive ions and non-reactive ions.

The etching rate $ER_{ionassisted}$ by the ion assist reaction at the point P is represented by the formula (8).

[Formula 8]

$$ER_{ion\ assisted}(P) = \frac{1}{\rho}\sum_i\sum_j\int_0^{\epsilon_{max}} Y_{ij}^{ion\ assisted}(\epsilon)F_i(P,\epsilon)\theta_j(P)d\epsilon \quad (8)$$

In the formula, $\epsilon_{max}$ is the maximum energy of incident ion. $Y_{ij}^{ionassisted}(\epsilon)$ is the yield at which the radical j by the ion i is desorbed from a surface reaction layer. $F_i(P, \epsilon)$ is the flux of the incident ion i having the energy $\epsilon$ at the point P. $\theta_j(P)$ is a substrate occupation rate of the radical j at the point P. $ER_{ionassisted}$ is a sum of both ions i of the reactive ions and non-reactive ions and a sum of entire radical j including the substrate surface material.

The deposition rate DR can be decomposed as shown in the formula (9). The first term of the right side of the formula (9) represents a deposition rate due to the accumulation effect of the deposition substance. The second term of the formula (9) represents a deposition rate due to the effect by the deposition substance generated by the reaction between the incident radical and the radicals of the surface reaction layer. The third term of the formula (9) represents a deposition rate by the effect by the deposition substance desorbed from the surface reaction layer due to the ion assist reaction.

[Formula 9]

$$DR_{total}(P) = DR^{(1)}(P) + DR^{(2)}(P) - DR^{(3)}(P) \quad (9)$$

The deposition rate due to the accumulation effect by the deposition substance at the point P is represented by the formula (10).

[Formula 10]

$$DR^{(1)}(P) = \frac{1}{\rho_d}\sum_m\left[\sigma_{m0}(\epsilon)\theta_0(P) + \sum_k \sigma_{mk}(\epsilon)\theta_k(P)\right]F_m(P) \quad (10)$$

In the formula, $\rho_d$ represents the deposition layer density. $\sigma_{m0}(\epsilon)$ represents an adsorption rate between the radical m and the clean to-be-etched material film. $\sigma_{mk}(\epsilon)$ represents the adsorption rate between the radical m and the adsorption layer film of the radical k formed on the to-be-etched material film. $\epsilon$ represents the energy of the radical m.

As can be seen from the formula (10), the radicals k formed on the to-be-etched material film are added for all k substituted with the radicals m and m is added for all of the deposition substances.

The formula (11) shows the deposition rate caused by the effect by the deposition substance generated by the reaction at the point P between the incident radicals having the energy $\epsilon$ and the radicals at the surface reaction layer.

[Formula 11]

$$DR^{(2)}(P) = \frac{1}{\rho_d}\sum_m\sum_{l\neq m}\left[\sigma_{l0}^{(m)}(\epsilon)\theta_0(P) + \sum_{k\neq m}\sigma_{lk}^{(m)}(\epsilon)\theta_k(P)\right]F_l(P) \quad (11)$$

In the formula, $\sigma_{l0}^{(m)}(\epsilon)$ represents the generation rate at which the deposition substance m is generated by the reaction between the flying radicals l and the clean to-be-etched material film. $\sigma_{lk}^{(m)}(\epsilon)$ represents the generation rate at which the deposition substance m is generated by the reaction between the flying radicals l and the adsorption film layer of the radicals k formed on the to-be-etched material film.

The reaction at the point P caused when ions having the energy $\epsilon$ are incident and the deposition substance is desorbed from the surface reaction layer is generally called an ion assist reaction. The deposition rate based on the effect by this ion assist reaction is represented by the formula (12).

[Formula 12]

$$DR^{(3)}(P) = \frac{1}{\rho_d}\sum_m\sum_{l\neq m}\int_0^{\epsilon_{max}}\left[\sum_l Y_{im}^{(l)}(\epsilon)\right]\theta_m(P)F_i(P,\epsilon)d\epsilon \quad (12)$$

In the formula, $\rho_d$ represents the deposition layer density. $Y_{im}^{(l)}(\epsilon)$ represents the yield of the reaction product l desorbed from the surface reaction layer in consideration of the fact that the deposition substance m is decomposed to the radicals l.

Figure 6:
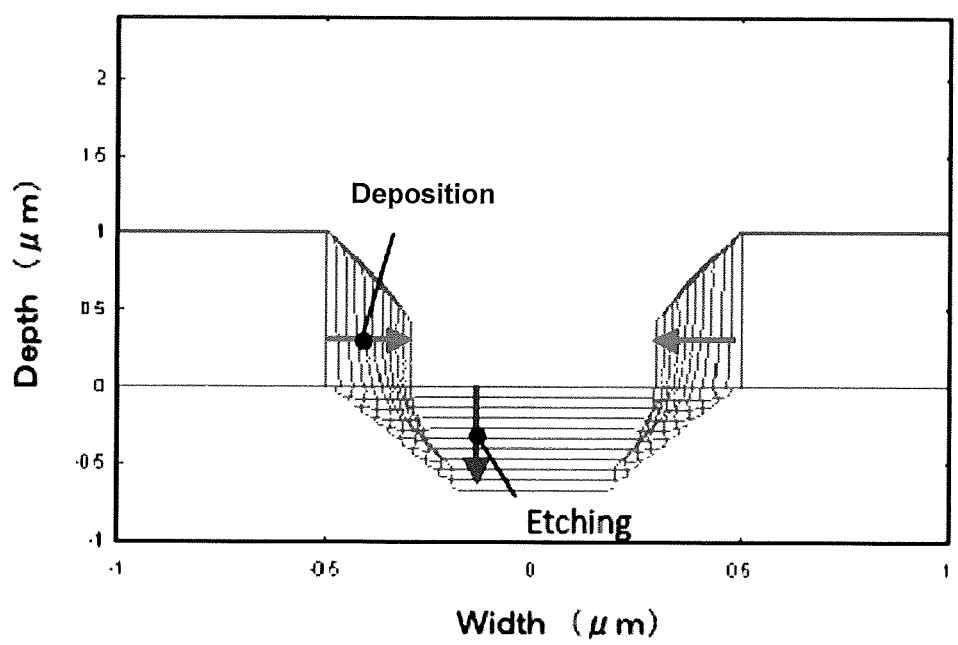
FIG. 6 is a view schematically showing a change of the shape calculated by the flow of FIG. 4.

Next, the transfer rate of each string P is calculated (STEP1-3). Specifically, when the difference between the etching rate and the deposition rate shows that the etching rate is higher than the deposition rate, then the etching is carried out. When the difference between the etching rate and the deposition rate shows that the etching rate is lower than the deposition rate on the other hand, then the deposition is carried out. Then, by connecting the string points describing the surface at an arbitrary time, the surface transfer rate can be calculated to thereby calculate the shape of the substrate surface at the arbitrary time. Thus, the result regarding the shape can be outputted and displayed (STEP1-4). FIG. 6 shows a change of the shape thus calculated.

[Calculation of Trajectories of Charged Particles and Calculation of Processing Surface Shape Considering Defect Due to Ultra-Violet Rays]

The following section will describe how the surface shape calculation unit 27 predicts the processing surface shape based on the calculation result provided from the trajectory calculation unit 26 and the surface shape calculation unit 27.

Figure 7A:
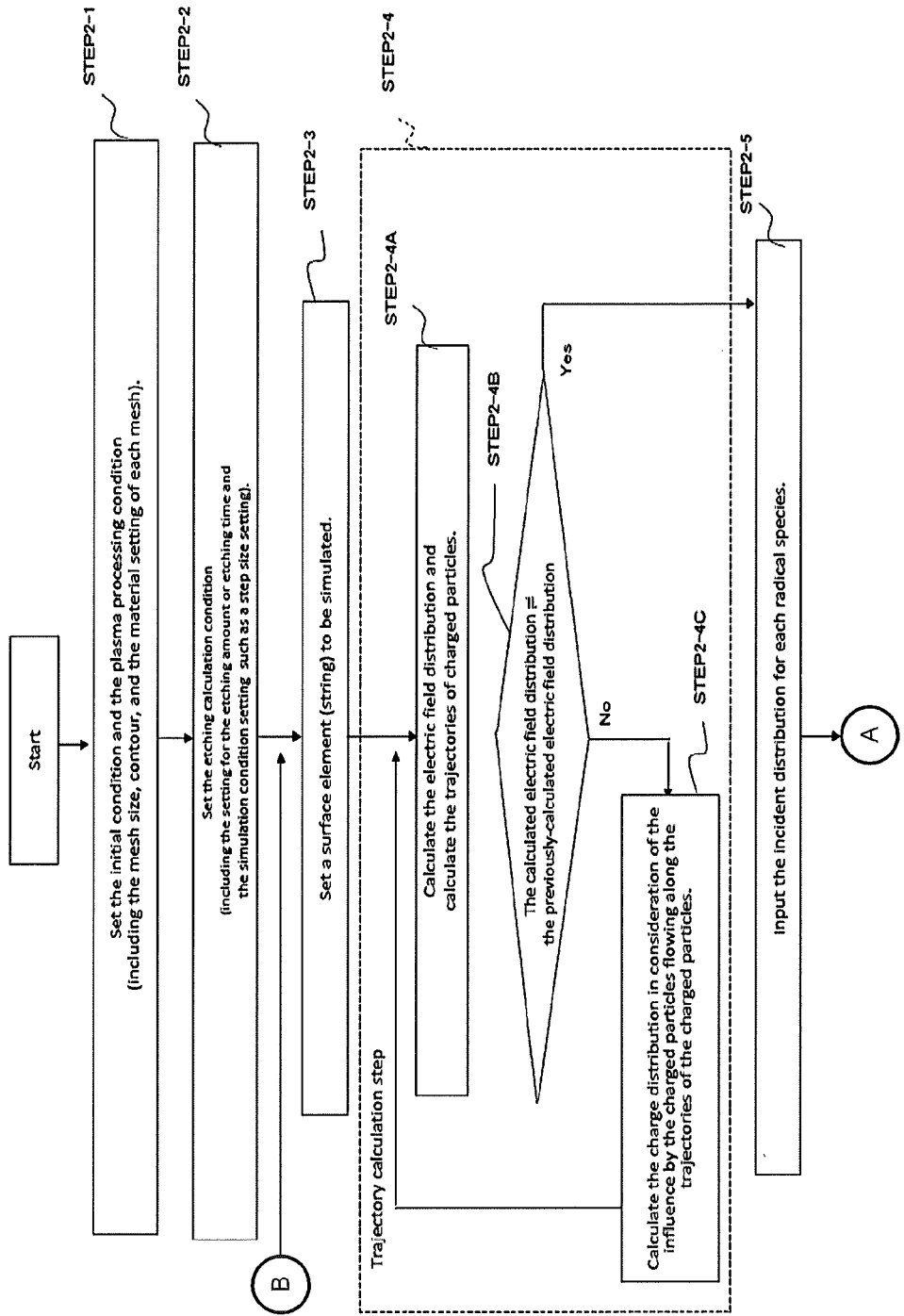
FIG. 7A is a view showing a part of the flow of the prediction method embodied by a program for predicting the processing shape by a plasma process according to the embodiment of the present invention.

FIG. 7A shows a part of the flow of the prediction method embodied by a program for predicting the processing shape by a plasma process according to the embodiment of the present invention. FIG. 7B illustrates the remaining part of the flow shown in FIG. 7A. In STEP2-1, when a simulation start step is started based on an input operation through the GUI 28, input data (e.g., initial value, boundary condition, property value) is referred in the above-described apparatus condition DB 21, the incident ion DB 22, the incident radical DB 23, the actual measurement DB 24, and the material property and surface reaction DB 25 as required. During this, the radical flux distribution is also set in advance. Specifically, regions of the substrate as a processing object for example are divided as a plurality of elements (meshes). Then, material types are set to the elements corresponding to the substrate regions. By setting the regions of a part as a mask, the regions of the processing surface are determined. During this determination, required data is obtained from the data stored in the material property and surface reaction DB 25.

In STEP2-2, the total etching time and a calculation step size are set. Alternatively, the assumed etching amount may be set instead of the total etching time.

Thereafter, the loop from STEP2-3 to STEP2-9 is repeated until STEP2-9 results in "yes".

The elements of the surface to be simulated (or strings when the shape is the two-dimensional one) are set (STEP2-3). Then, the processing proceeds to a trajectory calculation step (STEP2-4). In the trajectory calculation step, the trajectory calculation and the setting of the ion flux distribution are carried out, the details of which will be described below. Based on the actual measurement data (e.g., the current-voltage characteristic) inputted from the on-wafer monitoring sensor 11, the electron temperature and the electron density are calculated or the ion current and the sheath voltage are calculated. The substrate surface potential, the lower electrode potential, or the side wall resistance is measured. Thus, the calculation of the electron temperature and the electron density can provide the calculation of the sheath length and the sheath voltage. The calculation of the ion current and the sheath voltage on the other hand can provide the calculation of the sheath length. This actual measurement data is stored from the measurement 12 to the actual measurement DB 24. Thus, this data can be obtained from the actual measurement DB 24 or also can be directly obtained from the on-wafer monitoring sensor 11. Details for the calculation of the actual measurement data from the on-wafer monitoring sensor 11 will be described later.

The trajectory calculation unit 26 acquires, from the actual measurement DB 24, any or both of data (e.g., the electron temperature and the electron density) and data (e.g., the ion current and the sheath voltage). The trajectory calculation unit 26 also solves the Poisson equation based on the charge accumulation amount at the processing surface as a boundary condition to thereby calculate the electric field distribution to calculate the respective trajectories of the ions and electrons based on the Newton's equation of motion. In this embodiment, the electric field distribution is calculated. Thus, in consideration of the acceleration of charged particles due to the difference in the potential, the respective rates and travel directions of the ions and electrons can be accurately calculated.

Specifically, in STEP2-4A, the charge distribution of the processing surface is calculated based on an assumption that the incident ions and electrons have reached the processing surface. Then, the electric field distribution is calculated by solving the Poisson equation based on the charge accumulation amounts at the respective points at the processing surface as a boundary condition. Furthermore, based on the electric field distribution, the trajectories of the respective charged particles including the ions and electrons are calculated based on the Newton's equation of motion.

In STEP2-4B, it is determined whether the calculated electric field distribution is substantially the same as the previously-calculated electric field distribution or not. When it is determined that the former is not within the same range, it is determined that the respective ions and electrons flow based on the trajectories of the respective ions and the trajectories of the respective electrons. Then, a new charge distribution is calculated (STEP2-4C). Then, the processing returns to STEP2-4A. When it is determined that the electric field distribution calculated by STEP2-4B is substantially the same as the previously-calculated electric field distribution (i.e., it is determined that the electric field distribution is convergent), then the electric field distribution at the processing surface is steady. Thus, based on the trajectories and rates of the respective ions, the electric field distribution can be set as a function of the angle and energy regarding the ions incident on the respective points at the processing surface. This set function is stored in the incident ion DB 22. A sufficient amount of the trajectory calculation is preferably performed so as to sufficiently reduce a variation in the statistic amount. If a function already stored in the incident ion DB 22 is available, the function can be used by the trajectory calculation unit 26.

When an electric field distribution is calculated in the trajectory calculation step of STEP2-4, the actual measurement data of the surface potential and the bottom potential (the bottom potential also may be called a lower electrode potential) at the charge-up sensor modeling a processing face may be used to calculate, in consideration of the side wall resistance at the processing groove, the charge distribution of the processing groove surface based on which the electric field distribution is calculated. This calculation can also provide, when the processing face is similar to the trench structure of the charge-up sensor, the understanding of the behaviors of the electrons and ions in the groove in the charge-up sensor. Details of this will be described later.

The processing in STEP2-4 is mainly performed by the trajectory calculation unit 26. Thus, when the processing surface is flat, then the data for the respective ions and electrons incident on the processing surface can be set based on the actual measurement data of the on-wafer monitoring sensor 11. On the other hand, when the processing surface is concave due to the processing treatment promoted to a certain level, then it is possible to simulate how the surface processing is performed in consideration of how the trajectories of the ions and electrons incident on the concave shape are bent depending on the electric field distribution in the concave shape. In the embodiment of the present invention, when the processing surface is flat prior to the promotion of the processing, then the charged particles flowing from the upstream of the on-wafer monitoring sensor 11 can be equated with the charged particles flowing into the processing surface. Regarding the charges at the convex- and concave processing surface due to a promoted processing, the distribution of the charged particles is calculated by sequentially performing the calculation started from the flat surface in an initial state, thus providing realistic and accurate simulation.

By performing the trajectory calculation step of STEP2-4, the charged particles flowing into the processing surface can be considered. Neutral particles such as radicals and photons are separately calculated by a sensor and set for an input. Regarding neutral particles such as radicals, the incident distribution for each radical species is inputted by referring to the incident radical DB 23 using the energy and angle as a parameter (STEP2-5).

By the process as described above, charged particles and radicals for example incident on the processing surface from the outside are adsorbed by the processing surface or the adsorbed charged particles and radicals are desorbed from the processing surface. Regarding all types of particles involved in the surface reaction of the particles for example, the incident energy or the incident angle for example can be set.

Next, the surface reaction by the ion species and radical species thus set is calculated. The following section will describe the case where an influence by a defect caused by ultra-violet rays is considered.

In STEP2-6, exciting current is inputted from the UV sensor in the on-wafer monitoring sensor 11. Based on the exciting current, the UV spectrum is predicted. Based on the UV spectrum, the defect density near the processing surface is calculated.

This will be described specifically. First, in STEP2-6A, exciting current is inputted from the UV sensor in the on-wafer monitoring sensor 11. Based on the exciting current, the UV spectrum is calculated. In the embodiment of the present invention, the exciting current is associated with the UV spectrum by a neural network. Thus, the UV spectrum can be accurately calculated within a short time by the input of exciting current from the on-wafer monitoring sensor 11.

In STEP2-6B, upon receiving the input of the UV spectrum, the data stored in the property material and surface reaction DB 25 is used to calculate, based on the relation between the device structure and the UV absorption rate of the material, the distribution of the UV absorption amount absorbed in the substrate is calculated.

In STEP2-6C, based on the UV absorption distribution calculated in STEP2-6B, the defect density distribution due to the UV radiation in the substrate is calculated.

In STEP2-7, based on the defect density distribution calculated in STEP2-6, the adsorption rate and the desorption rate of the radical species or ion species to the processing surface and the activation energy for example are reset depending on the respective points on the processing surface. This resetting is performed by selecting the respective coefficients for the respective reactions stored in the material property and surface reaction DB 25. For example, the material property and surface reaction DB 25 may store the desorption rate, the adsorption rate, and the thermal excitation-type activation energy defined as a function of the defect density or also may store such a coefficient that is multiplied with a value applied when there is no defect.

In STEP2-8, based on the respective reaction coefficients at the respective points on the processing surface, the etching rate and the deposition rate are respectively calculated based on the ions incident on the respective points of the processing surface along the trajectories calculated in the trajectory calculation step and the incident flux distribution of the radicals based on the measurement by another method. Then, based on a difference between the etching rate and the deposition rate, the transfer transitions at the respective points of the surface are calculated.

The following section will describe the details of the surface transfer rate calculation step in STEP2-8. In STEP2-8A, based on the respective reaction coefficients at the respective points of the processing surface calculated in STEP2-7, the reaction between the surface material and the radicals at each processing surface as well as the reaction between the surface material and the ions are calculated repeatedly until each material has a steady coverage rate. As a result, the etching rate and the deposition rate are calculated, respectively. The etching rate is calculated, as shown in the above-described formula (5), as a sum of the etching rates by the thermal excitation-type chemical reaction, the physical sputtering, and the ion assist reaction, respectively. The deposition rate is calculated, as shown in the above-described formula (9), as a sum of the deposition rates by the accumulation effect of the deposition substance, the generation of the deposition substance, and the ion assist reaction. By calculating the respective rates in consideration of the respective coefficients of these reactions, the transfer transition of the processing surface is calculated in consideration of the defect by ultra-violet rays. Then, in STEP2-8B, the transfer transition of the processing surface is calculated based on a difference between the etching rate and the deposition rate.

Next, in STEP2-9, based on transfer rates at the respective points of the processing surface calculated in the surface transfer rate calculation step of STEP2-8, whether the processing amount or the processing time set under the processing conditions is satisfied or not is determined. When the processing amount or the processing time set under the processing conditions is not satisfied, the processing returns to STEP2-3 to reset the respective points at the processing surface. Then, the processing returns to the trajectory calculation step of STEP2-4. As shown in FIG. 7B, when the transfer amount of the surface calculated in STEP2-8 is higher than a predetermined etching amount (i.e., when the etching amount calculated in STEP2-8 does not reach the etching amount set in STEP2-2), the respective points of the surface are reset (STEP2-3) and the processing returns to STEP2-4 repeatedly. When the etching amount calculated in STEP2-8 reaches the etching amount set in STEP2-2 on the other hand, the loop is discontinued and the calculated surface shape data is outputted. The repetition of the loop processing also may be determined not based on the etching amount but based on the etching time.

If the processing in STEP2-6 is omitted and the resetting in STEP2-7 is omitted, the surface shape can be simulated without considering the defect by ultra-violet rays.

The following section will describe in detail the respective items described above.

[Ultra-Violet Sensor]

Figure 8:
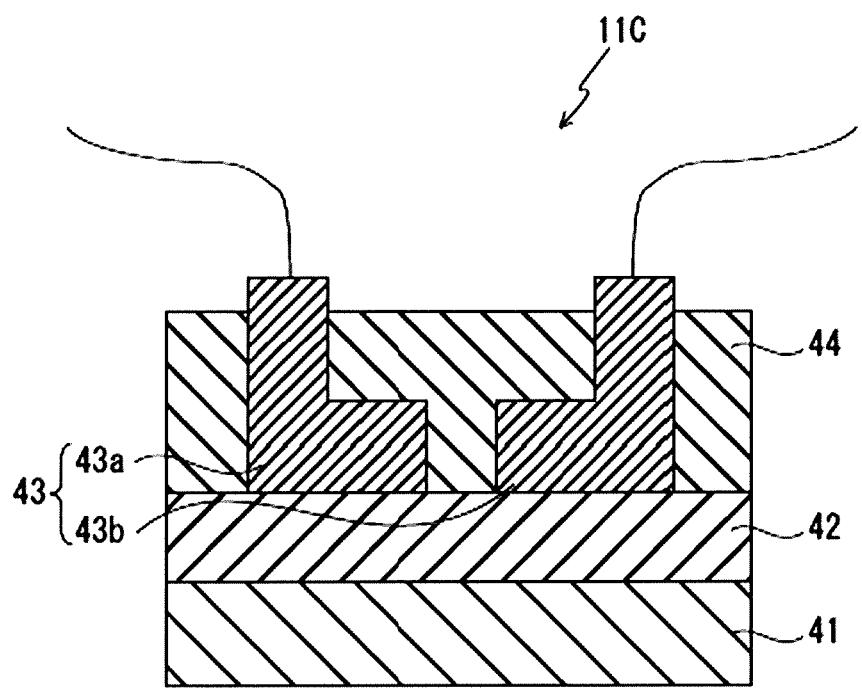
FIG. 8 is a cross-sectional view showing an ultra-violet sensor in an on-wafer monitoring sensor.

First, the following section will describe the ultra-violet sensor in the on-wafer monitoring sensor 11. FIG. 8 is a cross-sectional view schematically illustrating an example of the ultra-violet sensor 11C. The ultra-violet sensor 11C is configured, as shown, so that a silicon substrate 41 has thereon a silicon oxide film 42 as an insulator and the silicon oxide film 42 has thereon polycrystalline silicon films 43a and 43b having a predetermined pattern as an electrode and the polycrystalline silicon films 43a and 43b have thereon an insulator 44. The insulator 44 has a predetermined opening and is conductive with the polycrystalline silicon films 43a and 43b.

The ultra-violet sensor 11C is configured so that a plurality of units shown in FIG. 8 are arranged. The insulator 44 has different bandgaps. By the use of the insulator 44 of a silicon oxide film, since the silicon oxide film has a bandgap energy of 8.8 ev, when the ultra-violet sensor receives light having a ultra-violet wavelength of 140 nm or less corresponding to this bandgap, current flows between the polycrystalline silicons 43a and 43b as an electrode. By the use of the insulator 44 of a silicon oxide film, no current flows even when the ultra-violet sensor receives light having a wavelength of 140 nm or more. When the insulator 44 of a silicon nitride film is used and when the ultra-violet sensor receives the light having a wavelength of 250 nm or less, current flows. When the insulator 44 has a layered structure composed of a silicon nitride film and a silicon oxide film, current flows when the ultra-violet sensor receives the light having a wavelength of 250 nm or more.

As described above, when two or more ultra-violet sensors 11C are used and the same plasma is emitted, different currents flow in the respective sensors depending on the spectra of ultra-violet rays emitted from the plasma. In the embodiment of the present invention, by using the characteristic as described above, ultra-violet radiation spectra are calculated based on the current values of a plurality of ultra-violet sensors having different insulators 44.

[Method of Calculating Ultra-Violet Radiation Spectrum]

The following section will describe a method of calculating the ultra-violet radiation spectrum. Plasma is irradiated to the ultra-violet sensor unit. The ultra-violet sensor unit consists of the ultra-violet sensor 11C composed of one silicon oxide film layer as the insulator 44, the ultra-violet sensor 11C composed of one silicon nitride film layer as the insulator 44, and the ultra-violet sensor 11C composed of a layered structure of silicon nitride film and silicon oxide film as the insulator 44. Then, the ultra-violet radiation spectra are calculated based on the current values flowing in the respective ultra-violet sensors 11C.

This calculation requires a learning process in advance as described below. First, when plasma is irradiated to three types of ultra-violet sensor units having the different insulators 44 for example, current flowing in the respective ultra-violet sensors 11C is measured. The same plasma is measured by the ultra-violet spectroscope. Then, the light of a ultra-violet lamp having a known ultra-violet intensity is measured by an ultra-violet spectroscope. Based on these results, the ultra-violet radiation spectrum measured by the ultra-violet spectroscope can be converted to an absolute light intensity (e.g., photon/(cm² second)). By this method, a data set is prepared that is composed of the current values detected by the respective ultra-violet sensors 11C with regard to the respective types of plasmas and the absolute light intensity ultra-violet radiation spectrum. After the data set is prepared, a feed forward neural network is used to configure the system.

Figure 9:
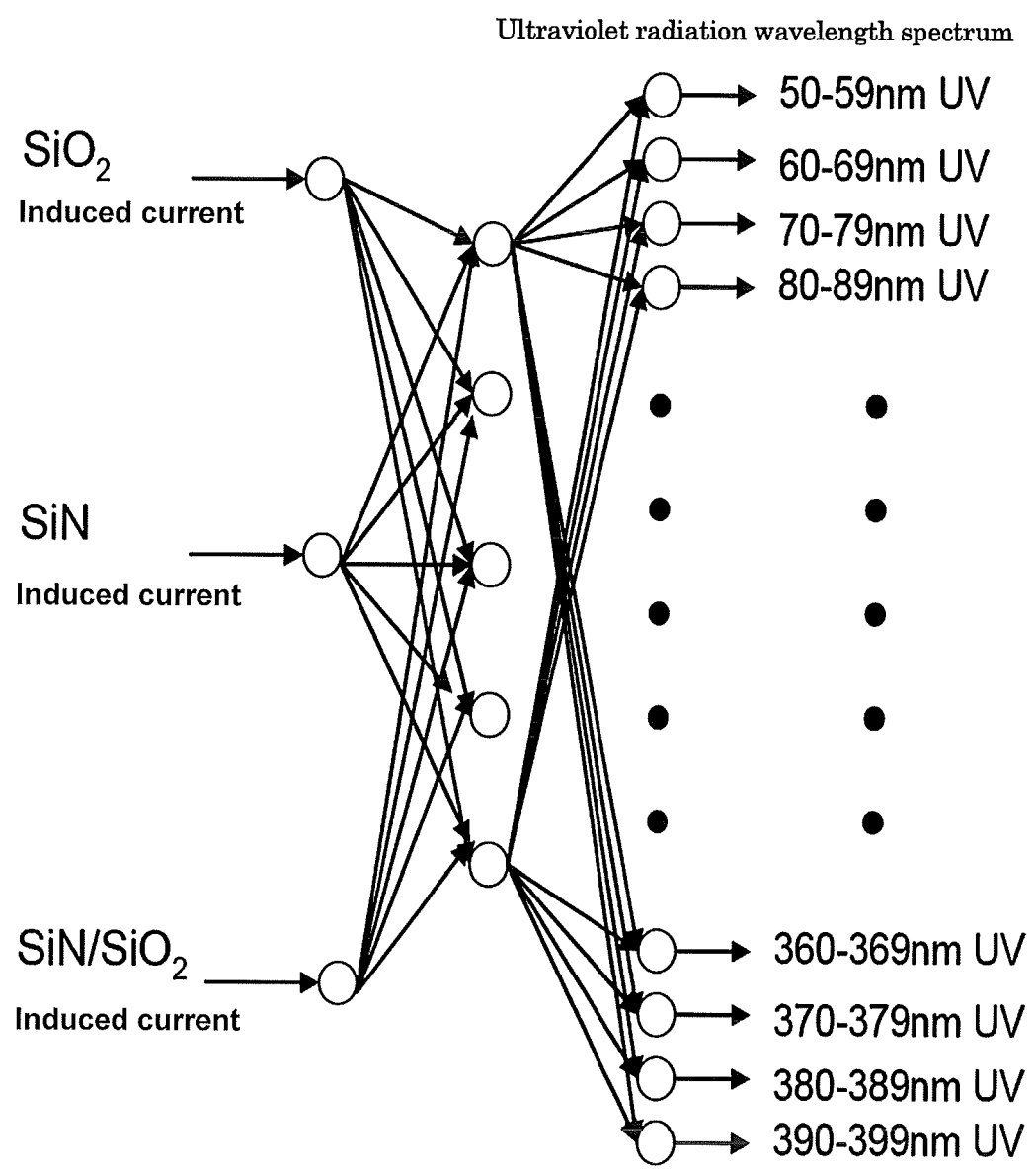
FIG. 9 is a view schematically showing a neural network to acquire ultra-violet radiation spectrum from the data measured by ultra-violet sensor.

FIG. 9 illustrates the outline of the neural network. As shown in FIG. 9, it is assumed that an input is sensor current and an output is an absolute light intensity ultra-violet radiation spectrum. Based on the data set, the weighting of the neural net is determined. The output may be a standardized value or a normalized value or also may be a value subjected to a calculation processing by a certain function. When a plasma light emission line is known, the wavelength of the light emission line also may be used as an output of the neural net.

Next, the neural network system as shown in FIG. 9 is used to calculate the ultra-violet radiation spectrum. After the learning in the system is done, the ultra-violet radiation spectrum can be used in any plasma processing apparatus 10.

An example will be described below. First, three types of ultra-violet sensors 11C are placed in the chamber 15 for which an ultra-violet radiation spectrum is desired to be measured and plasma is generated by discharge. Then, when the current outputted from the ultra-violet sensors 11C is measured and is inputted to the neural network system, the neural network outputs the absolute intensity of the ultra-violet radiation spectrum.

In order to confirm the accuracy of the measurement by the ultra-violet sensor, the three types of ultra-violet sensors 11C are stored in the chamber and argon, 3 fluoromethane iodide, and 8 fluoromethane cyclobutane are introduced to the chamber so that a pressure of 0.7 Pa is reached. Then, an inductive coupling-type plasma source was used to generate plasma. Based on the measurement data by the three types of ultra-violet sensors 11C, the light emission spectrum was calculated by the above method. On the other hand, the plasma in the chamber was separately measured by an ultra-violet spectroscope. The light emission spectra obtained by any of the measurements were substantially the same to one another, thus showing that this method was correct.

In the above-described description, the three types of ultra-violet sensors 11C were used. However, two or four types of ultra-violet sensors 11C also may be used. In addition to gaseous species such as argon or fluorocarbon gas, other halogens (e.g., chlorine, bromine) or various gases such as hydrogen or nitrogen also may be used.

[Calculation of Ultra-Violet Irradiation Damage]

The following section will describe a method of calculating the ultra-violet irradiation damage caused in a semiconductor device based on the above-described ultra-violet intensity spectrum. This calculation method can be divided to a process of calculating the absorption amount of ultra-violet rays and a process of calculating a damage amount.

Figure 10:
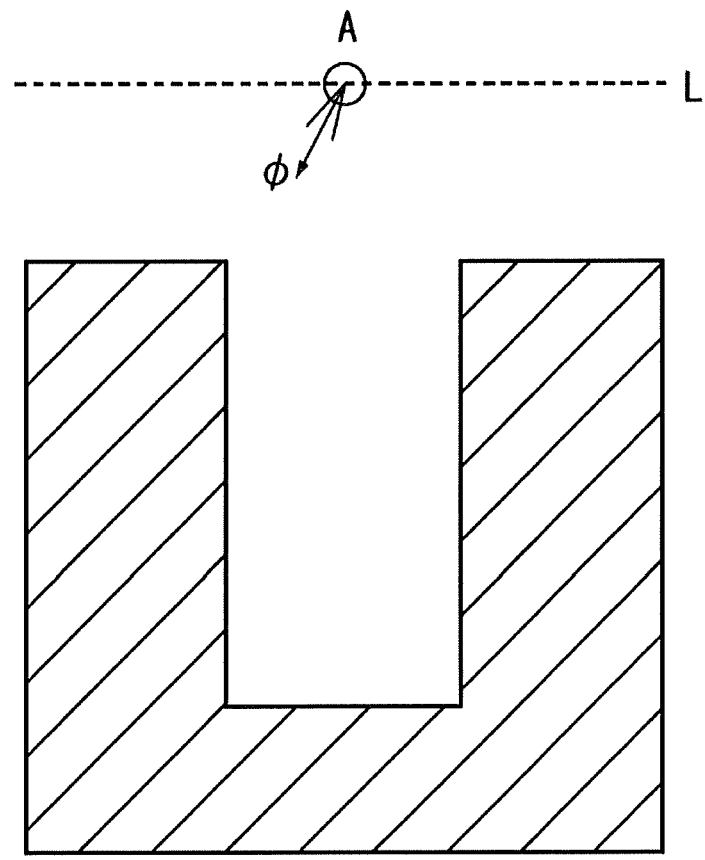
FIG. 10 is a view showing a device structure for a model to calculate ultra-violet irradiation damage.

The following section will describe the process of calculating the ultra-violet absorption amount. For example, as shown in FIG. 10, a device structure as a model is firstly set. The following section will describe a case where the damage in a single layer film consisting of a silicon oxide film is calculated. Light entering the device from a position sufficiently away from the device (the dotted line L in the figure) is calculated. Specifically, when it is assumed that the ultra-violet amount emitted at the point A on the position L is $\Gamma$, the light proceeding along the solid angle $\phi$ can be represented as $\Gamma/2\pi\times\phi$. When assuming that this light intensity is $\Gamma_1$ and the absorption efficiency of the material in the device is $A(\lambda)$, then this light is absorbed in the device based on the formula (13). In the formula, $\lambda$ represents a wavelength of the ultra-violet rays.

[Formula 13]

$$\frac{d\Gamma_1}{dx} = -A(\lambda) \tag{13}$$

By using this method to calculate the trajectories of the ultra-violet rays from any points at the position L, the ultra-violet light intensity absorbed to the device can be calculated.

Here, the present inventors have found that the absorbed ultra-violet spectrum and the defect caused in the insulator (E'Center) have therebetween the relation as shown below.

[Formula 14]

$$\frac{\partial n}{\partial t} = \int f_{damage} \phi d\lambda - \frac{n}{\tau} \tag{14}$$

In the formula, n represents a defect density, t represents time, $\phi$ represents an ultra-violet absorption amount, $\lambda$ represents an ultra-violet wavelength, $\Gamma$ represents a time constant, and f represents a defect generation coefficient. A relation of $f=3.21(\lambda-105.0)+25.0$ is established.

By using the formula (14), based on the ultra-violet intensity absorbed in the device, the defect density caused in the device material can be calculated. The distribution of the defect density in the depth direction thus calculated was confirmed to well correspond to the distribution of the defect density in the depth direction measured by the electron spin resonance technique.

This technique can be applied even when the shape changes in the case of the etching for example. By changing the position at which the absorption of irradiated light occurs in accordance with the change of the shape, the defect density formed with the progress of the etching can be calculated with the progress of time.

Thus, the ultra-violet sensor 11C can be used to calculate the ultra-violet radiation spectrum and the defect distribution can be calculated based on this ultra-violet radiation spectrum. Specifically, based on the information of current values outputted from a plurality of ultra-violet sensors 11C and the device structure and the process time for example, the defect density caused in the device can be calculated in a quantitative manner.

[Application of Ultra-Violet Radiation Spectrum]

Alternatively, the ultra-violet sensor 11C also can be used to calculate the ultra-violet radiation spectrum to calculate the deterioration of the electrical characteristic of the semiconductor device. A relation is identified in advance between the ultra-violet radiation spectrum and the deterioration of a transistor. Using the neural network for example, the relation is identified between the ultra-violet radiation spectrum and the charge pumping current of the transistor. Since the charge pumping current shows a value corresponding to the defect and the interface state of the interface between the silicon oxide film and the silicon substrate, the charge pumping current is frequently used to measure the interface state.

First, the transmitted light intensity is calculated. As in FIG. 10, a device structure as a model is set. When the light trajectory is calculated, light of what wavelength is irradiated to the transistor at the core of the device can be known. For example, as a model, a single layer film consisting of silicon oxide film is assumed. Using the above-described neural net, the information of light irradiated to the transistor section can be used to calculate the deterioration amount of the transistor.

When the calculation result of the charge pumping current when the 3 fluoromethane iodide plasma was emitted to the MOS device was compared with the current value actually measured by the charge pumping technique, a good correspondence was found.

By the fact as described above, the defect density caused in the transistor can be calculated in a quantitative manner based on the information of the current values outputted from a plurality of ultra-violet sensors 11C as well as the device structure and the process time for example.

In the embodiment of the present invention, as described above, three types of ultra-violet sensors 11C composed of a single layer of a silicon oxide film, a single layer of a silicon nitride film and a layer structure of a silicon nitride film and a silicon oxide film respectively are used to measure the current that flows when these ultra-violet sensors 11C are subjected to ultra-violet rays. Then, a neural network is established in advance based on the database in which the relation between the current value and the ultra-violet radiation spectrum is accumulated. Thus, the ultra-violet radiation spectrum can be introduced during measurement only based on the current signal from the sensor.

The following section will describe the calculation of the ultra-violet irradiation damage. When the insulator 44 in the ultra-violet sensor 11C receives ultra-violet rays, the rate at which a defect is caused in the insulator 44 is a function of the ultra-violet intensity and the ultra-violet wavelength. It is known that the density of the defect saturates at a certain time constant of about a few dozens of seconds. Thus, the defect density when ultra-violet irradiation is caused is calculated.

[Sensor for Sheath Monitoring of On-Wafer Monitoring Sensor]

By the sensor for sheath monitoring in the on-wafer monitoring sensor 11, the electron temperature and the electron density are measured. Based on the measurement result, the sheath length and the sheath voltage can be calculated. Alternatively, the sensor for sheath monitoring can be used to measure the ion current and the sheath voltage based on the result of which the sheath length can be calculated.

As shown in FIG. 1, the on-wafer monitoring sensor 11 is placed in the chamber 15 in the plasma processing apparatus 10 and the measurement is performed under the same conditions as those used to etch the sample.

Figure 11:
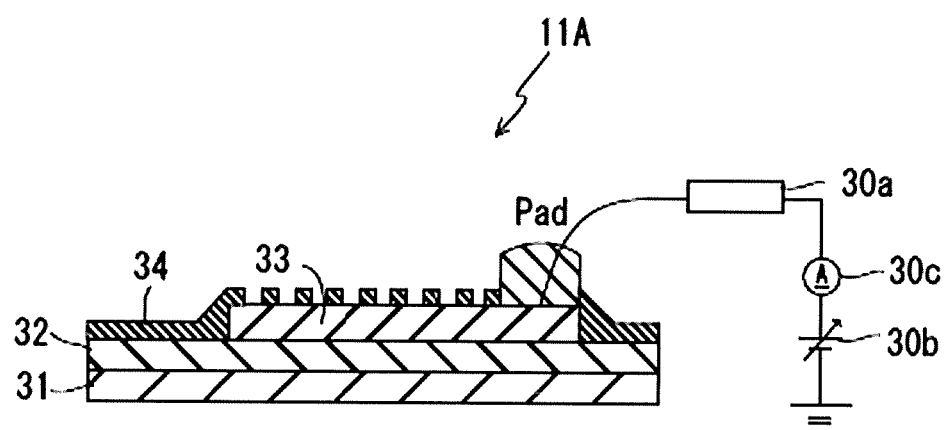
FIG. 11 is a schematic cross-sectional view of a sensor for sheath monitoring in an on-wafer monitoring sensor.

As shown in FIG. 1, the on-wafer monitoring sensor 11 is placed in the chamber 15 of the plasma processing apparatus 10 and the measurement is performed under the same conditions as those used to etch the sample. FIG. 11 is a cross-sectional view schematically illustrating one example of the sensor for sheath monitoring 11A in the on-wafer monitoring sensor 11. As shown in FIG. 11, a silicon substrate 31 has thereon a silicon oxide film 32. The silicon oxide film 32 has thereon an Al electrode 33 having a predetermined pattern. The Al electrode 33 has thereon an $Al_2O_3$ film 34 including many holes of 0.3 microns for example. This sensor for sheath monitoring 11A is placed under substantially the same circumstance as that in which a substrate is subjected to a plasma processing. The measurement 12 of the sensor for sheath monitoring 11A (see FIG. 1) will be described below. Specifically, when a substrate subjected to a plasma processing is in a floating state, as shown in FIG. 11, the Al electrode 33 is connected to a DC power supply 30b as a measurement power supply via a filter 30a as required. An output voltage from the DC power supply 30b is applied in a changeable manner and the current flowing in the Al electrode 33 is measured by a measurement 30c. When the substrate subjected to a plasma processing is applied with a dc bias or an RF bias, the measurement 12 of the sensor for sheath monitoring 11A has a measurement power supply configured by any or both of a DC power supply and a high-frequency power supply. The measurement power supply is connected to the Al electrode 33 via a wiring and a DC component in the current flowing in the wiring is measured via a filter.

First, the following section will describe, when a substrate subjected to a plasma processing is placed in a floating state, how to obtain the information regarding the current measurement by the charged particles of the substrate surface and the sheath.

In this case, it can be assumed that the sheath on the substrate is based on Child's Law. Flowing current changes depending on the voltage applied to the substrate. When the substrate voltage is lower than the floating potential (floating potential), then electrons are rejected from the electric field and only ions flow in the substrate. When the substrate voltage is higher than the floating potential and is lower than the plasma potential (i.e., the plasma space potential), both of ions and electrons flow in the substrate. When the substrate potential is higher than the plasma potential, no ions flow in the substrate and only electron current flows therein. Thus, by changing the voltage of the Al electrode as a lower electrode of the sensor for sheath monitoring 11A to measure the current-voltage characteristic, the electron density, the electron temperature, and the sheath length in the plasma can be calculated.

Figure 12:
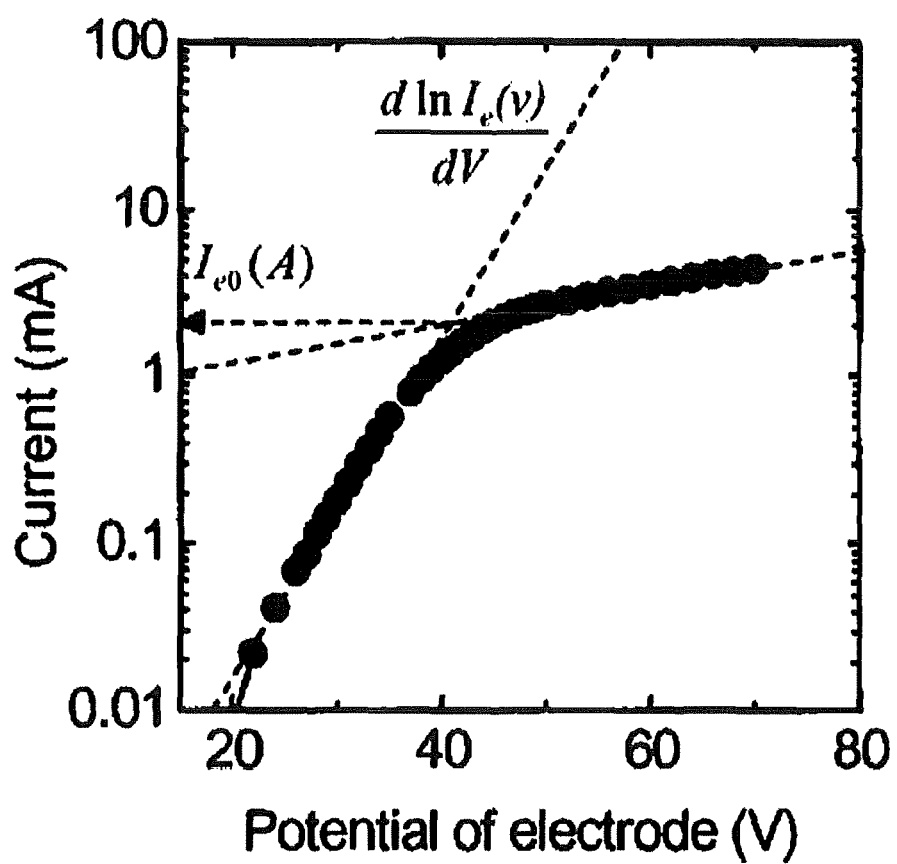
FIG. 12 is a view showing a IV characteristic of a sensor for sheath monitoring.

FIG. 12 is a schematic view illustrating the current-voltage characteristic obtained from the sensor for sheath monitoring 11A. In FIG. 12, the horizontal axis shows the electrode potential (V) represented by a linear scale and the vertical axis shows the current (mA) shown by a log scale. As shown in FIG. 12, based on the inclination of the current-voltage characteristic, the electron temperature can be calculated. Based on the saturate electron current, the electron density can be calculated. The electron density and the electron temperature thus calculated include the important information near the substrate.

Specifically, the voltage at which current is 0 A (i.e., the electron current equals to the ion current) is a floating potential $V_f$. In the graph shown in FIG. 12, the plasma potential $V_p$ is calculated based on the coordinate on the horizontal axis at the intersection point of the straight line obtained by approximating the low voltage side and the straight line obtained by approximating the high voltage side. Based on the coordinate on the vertical axis of the intersection point, the electron current $I_{eo}$ is calculated. Based on the formula (15) and the formula (16), the electron temperature $n_e$ and the electron density $T_e$ are calculated.

[Formula 15]

$$\frac{d \ln I_e}{dV} = -\frac{e}{kT_e} \quad (15)$$

[Formula 16]

$$N_e(\text{cm}^{-3}) = 3.73 \times 10^{11} \frac{I_{e0}(A)}{S(\text{cm}^2)[T_e(\text{eV})]^{1/2}} \quad (16)$$

In the formulae, e represents an elementary charge, k represents a Boltzmann constant, and S represents an electrode area.

Based on the electron temperature and the electron density calculated by the formula (15) and the formula (16), the sheath length s and the sheath voltage $V_0$ are calculated using the formula (17) to the formula (19). $\lambda_{De}$ represents a Debye length.

[Formula 17]

$$s = \frac{\sqrt{2}}{3} \lambda_{De} \left(\frac{2V_0}{T_e}\right)^{3/4} \quad (17)$$

[Formula 18]

$$\lambda_{De} = \left(\frac{\varepsilon_0 T_e}{eN_e}\right)^{1/2} \quad (18)$$

[Formula 19]

$$V_0 = V_p - V_f \quad (19)$$

Regarding the formula (19), the fact that a bias voltage is applied to the substrate (i.e., the on-wafer monitoring sensor 11) is considered by adding a bias voltage $V_{bias}$ for example in an actual case.

The following section will describe how to obtain the information for the current measurement by the charged particles at the substrate surface and the sheath by describing a case where a bias is applied to a substrate subjected to a plasma processing by an example of the application of an RF bias.

Figure 13:
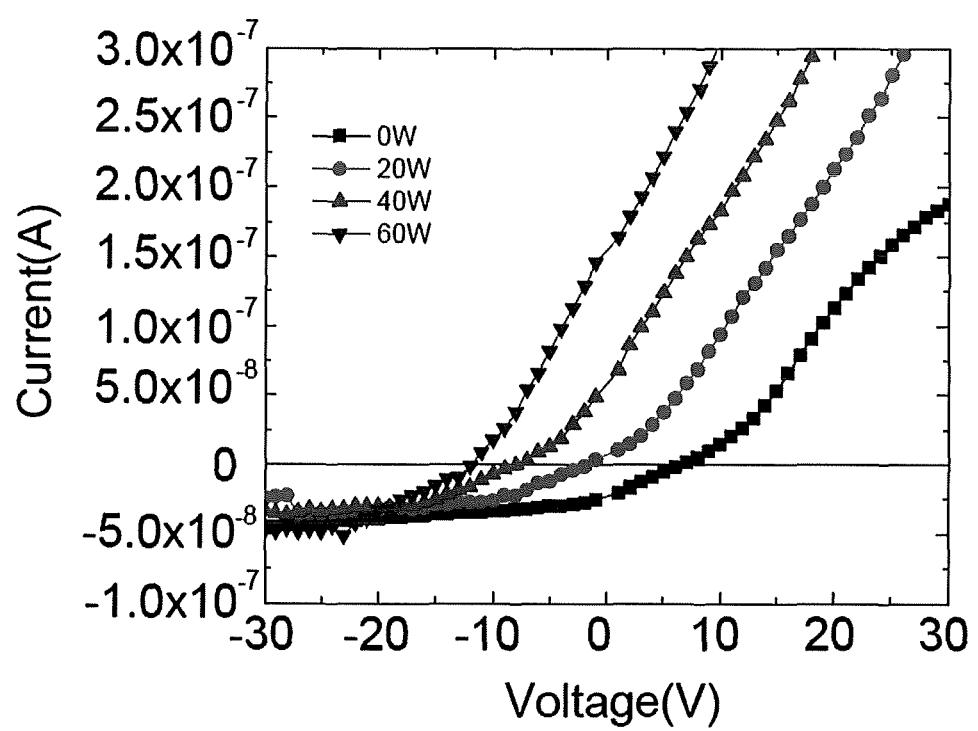
FIG. 13 is a view showing a current-voltage characteristic when a sensor for sheath monitoring as shown in FIG. 11 is used to apply an RF bias to the Al electrode as a lower electrode.

FIG. 13 illustrates a current-voltage characteristic when the sensor for sheath monitoring 11A as shown in FIG. 11 is used to apply an RF bias to the Al electrode 33 as a lower electrode. In FIG. 13, the horizontal axis represents the DC component of an applied voltage while the vertical axis represents the DC component of current. Any of these axes is represented based on the linear scale. In FIG. 13, the respective plots represented by ■, ●, ▲, and ▼ are classified based on the magnitude of the high-frequency power and show, in this order, when no high-frequency wave as well as 20 W, 40 W, and 60 W of high-frequency power are applied.

As can be seen from FIG. 13, with an increase of the high-frequency power, the current voltage shows such a waveform that shifts in the negative voltage direction. The reason is that, when the lower electrode (i.e., the Al electrode 33) is applied with an RF bias, then the substrate includes therein a DC auto-bias. In this case, the sheath on the substrate is not based on the Child's Law and thus must be considered as a DC high voltage sheath. Thus, the formula (17) cannot be used to calculate the sheath length.

When the substrate includes therein an auto-bias, electrons are reflected at an end of the sheath and thus do not exist in the sheath. Thus, the electron current can be approximated as zero. On the other hand, ions pass through the sheath while being accelerated by the sheath voltage to reach the substrate. By solving the continuity equation for the ion current density $J_0$ and the Poisson equation using the energy conservation law, the formula (20) is obtained as the ion current density $J_0$.

[Formula 20]

$$J_0 = \frac{4}{9} \varepsilon_0 \left(\frac{2e}{m_i}\right)^{\frac{1}{2}} \frac{V_0^{\frac{3}{2}}}{s^2} \quad (20)$$

The formula (20) is essentially the same as the formula of Child-Langmuir. This means that the space charge effect by ions is handled instead of that by electrons. The formula (20) can be used to obtain the formula (21).

[Formula 21]

$$s = \frac{2V_0^{\frac{3}{4}}}{3} \sqrt{\frac{\varepsilon_0}{J_0}} \left(\frac{2e}{m_i}\right)^{\frac{1}{4}} \quad (21)$$

In the formula (20) and the formula (21), s represents the sheath length (m), $J_0$ represents the ion current density (A/m$^2$), $m_i$ represents the ion mass (kg), and $V_0$ represents the sheath voltage (V).

When no RF bias is applied, the sheath voltage can be calculated based on a difference between the plasma potential and the floating potential. When an RF bias is applied on the other hand, the sheath voltage includes not only the sheath voltage in the floating state but also the auto-bias voltage. Thus, the sheath voltage can be calculated based on the formula (22).

[Formula 22]

$$V_0 = V_p - V_f - V_{shift} \quad (22)$$

In the formula, the shift amount $V_{shift}$ can be calculated based on how much the current-voltage waveform during the application of an RF bias shifts in the negative voltage direction when compared with the current-voltage waveform without the application of an RF bias. When the auto-bias voltage is much higher than the electron temperature, then the measurement voltage may be assumed as the sheath voltage $V_0$.

The ion saturate current density $J_0$ can be calculated by dividing, by the electrode area, a region in the current-voltage waveform when a negative voltage is applied (i.e., a current value in an ion saturate current).

Thus, based on the calculated sheath voltage $V_0$ and ion saturate current density $J_0$, the sheath length s can be calculated based on the formula (21). The formula (21) is obtained by the above-described model. Thus, the invention is not always limited to this formula. Another sheath model also may be used.

When an RF bias is applied, the electron density and the electron temperature cannot be calculated from the current-voltage characteristic shown in FIG. 13 and only the sheath length is calculated. Thus, if information is required for the plasma electron density or the electron temperature, then the Al electrode 33 as a lower electrode is caused to be in a floating state and the current-voltage waveform is measured. Then, the electron density and the electron temperature can be measured as in the above-described case where the substrate is in a floating state.

[Charge-Up Sensor of On-Wafer Monitoring Sensor]

Figure 14:
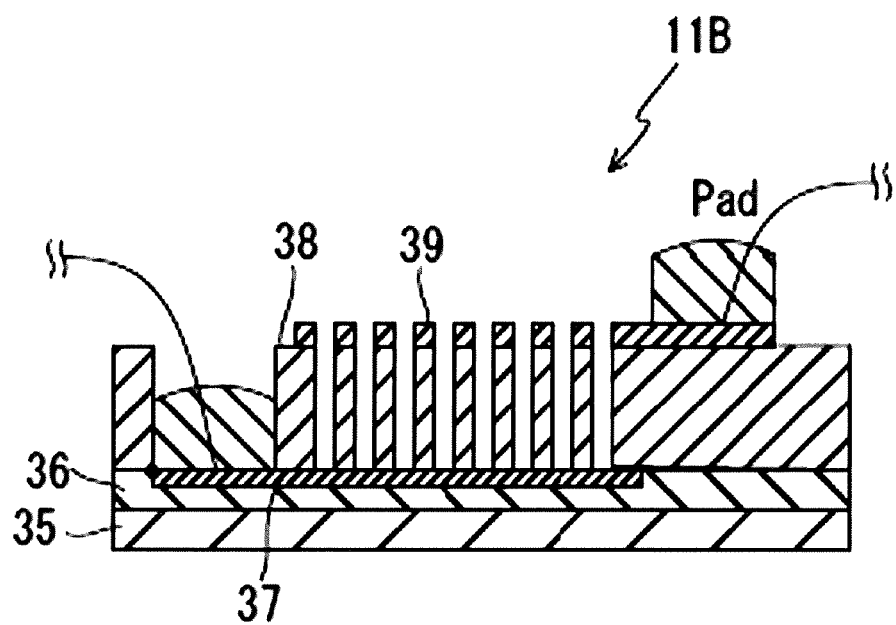
FIG. 14 is a schematic cross-sectional view of a charge-up sensor of an on-wafer monitoring sensor.

FIG. 14 is a cross-sectional view schematically illustrating the charge-up sensor 11B of the on-wafer monitoring sensor 11. The entirety of the charge-up sensor 11B has a layered structure. As shown in FIG. 14, this charge-up sensor 11B has a layered structured as described below. Specifically, a silicon substrate 35 has thereon a silicon oxide film 36. The silicon oxide film 36 has thereon a first polycrystalline silicon film 37 having a predetermined pattern. The first polycrystalline silicon film 37 has thereon a silicon oxide film 38 having a predetermined groove. The silicon oxide film 38 has thereon a second polycrystalline silicon film 39. The charge-up sensor 11B includes therein many holes penetrating the polycrystalline film 37 and the silicon oxide film 38. These holes have a diameter of 0.1 microns for example. The existence of the charge-up sensor 11B in the plasma process prevents electron having an isotropic rate distribution from reaching the lower electrode and allows ions accelerated by the substrate to reach the lower electrode. Thus, the substrate surface and the lower electrode have different potentials. By measuring the potential of the first polycrystalline silicon film 37, the potential of the lower electrode can be calculated. By measuring the potential of the second polycrystalline silicon film 39, the potential of the surface can be calculated.

Figure 15:
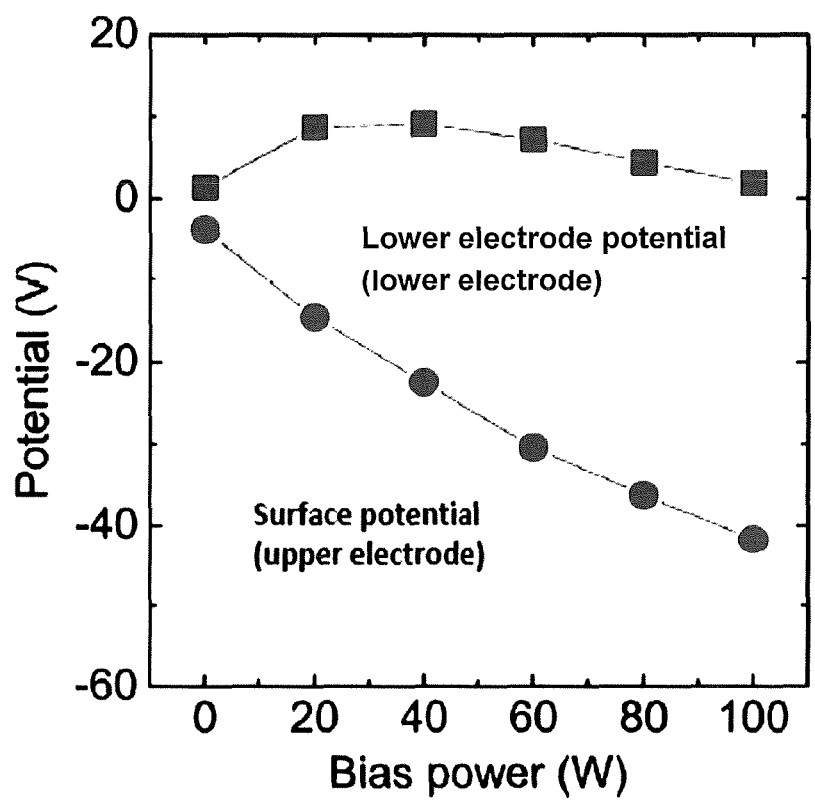
FIG. 15 is a view showing an example of the actual measurement about a high-frequency power dependency of a surface potential calculated by charge-up sensor (i.e., the potential of the second polycrystalline silicon film) and a lower electrode potential (i.e., the potential of the first polycrystalline silicon film).

FIG. 15 shows an example of the actual measurement illustrating the high-frequency power dependency of the surface potential calculated by the charge-up sensor 11B (i.e., the potential of the second polycrystalline silicon film 39) and the lower electrode potential (i.e., the potential of the first polycrystalline silicon film 37). By using the charge-up sensor 11B, unevenly-distributed potentials in a minute structure can be measured in a quantitative manner.

[Calculation of Sheath Potential Distribution]

As described above, based on the sheath length calculated by the formula (17), an analysis region for the potential calculation is determined. Then, the sheath potential is calculated based on the sheath voltage as a boundary condition. Specifically, analysis regions are set as an upper region from the substrate surface to the sheath length and a lower region in which a minute pattern is formed.

[Trajectory Calculation]

Next, based on the Monte Carlo simulation technique, the trajectories of the particles are calculated. Based on the sheath potential distribution calculated in the manner as described above, the trajectories of the ion particles are calculated. The particles are incident in a vertical direction from the upper end of the sheath down to the substrate and are accelerated in accordance with a given potential distribution. Then, the trajectories are bent and the particles impinge on the lower substrate of the analysis region.

The initial rate $u_{ion}$ of the particles is determined based on the Bohm rate obtained from the formula (23) based on the electron temperature acquired from the actual measurement.

[Formula 23]

$$u_{ion} = \sqrt{\frac{kT_e}{m_{ion}}} \qquad (23)$$

Based on the calculated particle trajectory, the incident angle at which the particle impinges on the substrate at each position is calculated.

Based on the distribution of the ion substrate incident angles and the energy distribution, plasma etching simulation is performed. This simulation is carried out so that an influence by the ion trajectory bent due to the sheath potential distribution is reflected on the angle distribution of the ion incident flux. Thereafter, the plasma etching simulation is performed based on the procedure as described above.

EXAMPLE

The following section will describe an embodiment of the present invention in further detail.

Figure 16:
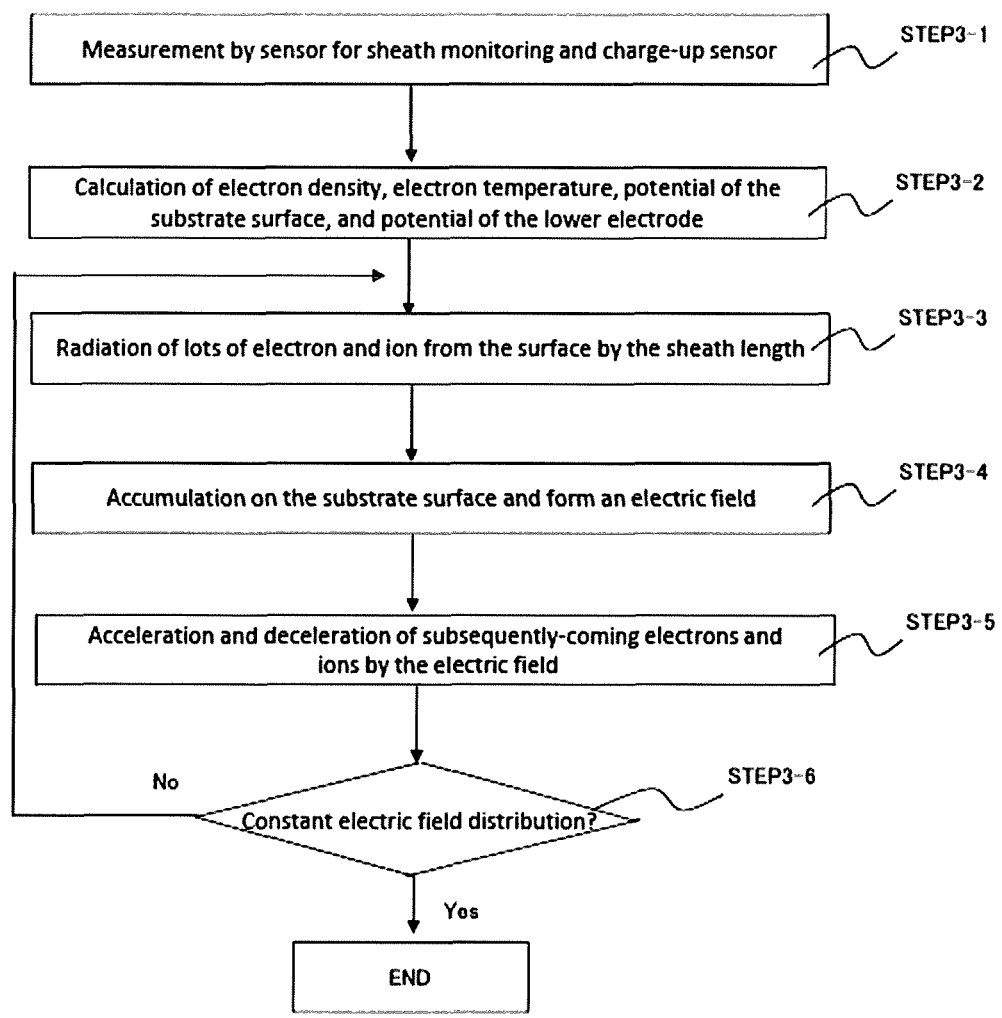
FIG. 16 is a flow diagram showing the procedure in the embodiment.

The sensor for sheath monitoring 11A and the charge-up sensor 11B were used to calculate the ion trajectory based on the information for the neighborhood of the substrate obtained from these electrical measurements. FIG. 16 is a flow diagram showing the procedure in the embodiment.

In STEP3-1 and STEP3-2, the sensor for sheath monitoring 11A is used to calculate the electron temperature and the electron density near the substrate. The charge-up sensor 11B is used to calculate the potential of the substrate surface and the potential of the lower electrode.

Figure 17:
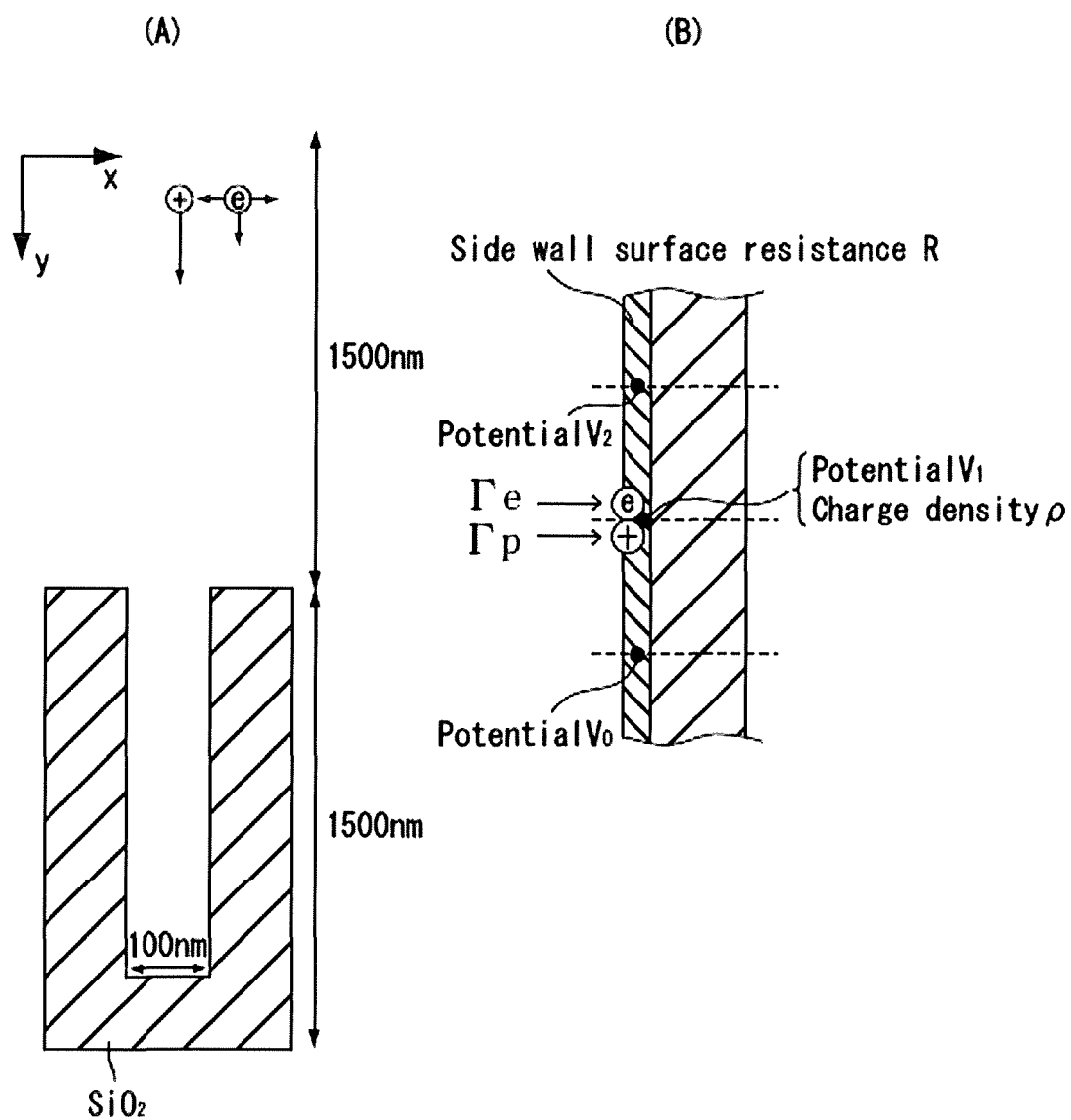
FIG. 17 (A) is a view showing a model provided to calculate an ion trajectory, and FIG. 17 (B) is a view showing an expansion of a side wall of a groove of FIG. 17(A).

A model as shown in FIG. 17 was set to calculate the ion trajectory. FIG. 17(A) illustrates the model provided to calculate the ion trajectory. FIG. 17(B) illustrates the expansion of the side wall of the groove of FIG. 17(A). Based on an assumption that the hole processing to the silicon oxide film is performed to achieve a hole diameter of 100 nm and a hole depth of 1500 nm so that the hole is axis-symmetric, the right half of FIG. 17(A) is calculated. Based on the electron temperature, the electron rate and the initial ion rate are calculated.

In STEP3-3, the first electron takeoff position is firstly determined as y=0 and x=random in FIG. 17. Next, the electron takeoff direction is determined randomly. The electrons move from the takeoff position along the electric field. Thus, the electron transfer until the electrons impinge on the pattern is calculated. The electrons having impinged on the pattern are accumulated at the position. Next, the first ion takeoff position is determined as y=0 and x=random in the figure. Ions having an initial speed move in a vertical direction to the substrate. Ions move from the takeoff position along the electric field. The transfer of the ions until the ions impinge on the pattern is calculated. The ions having impinged on the pattern are accumulated at the position.

In STEP3-4, the electric field due to the accumulated electrons or ions is calculated and the electric field is changed. Thereafter, subsequently-coming electrons and ions are accelerated and decelerated by the electric field (STEP3-5).

Then, the transfer calculation and the electric field calculation are carried out alternately by performing the transfer calculation and the electric field calculation for the second electron and the second ion and the transfer calculation and the electric field calculation for the third electron and the third ion and the electric field calculation in this order for example. The transfer calculation and the electric field calculation for the charged particles are carried out until no more change in the electric field is found after the electric field calculation (STEP3-6).

Based on the electric field thus obtained, the ion trajectory can be calculated again to thereby calculate the ion trajectory in the minute structure. Since it is expected that the pattern side wall is conductive to a certain level, the side wall resistance can be assumed so that the potential of the lower electrode is adjusted to the actual measurement value, thus providing an ion trajectory having improved reliability.

Specifically, as shown in FIG. 17(B), the side wall of the hold in the silicon oxide film is divided to a plurality of elements and potentials are assumed for the respective surface element points. By using the charge-up sensor 11B shown in FIG. 14, the potential of the second polycrystalline silicon film 39 (this potential is generally called a processing surface potential) and the potential of the first polycrystalline silicon film 37 (this potential is generally called a bottom potential) can be measured as shown in FIG. 15. Thus, as shown in FIG. 17(B), it is assumed that the side wall has the side wall surface resistance R, the charge density is p and the potential is $V_1$ at a certain point (the first point) for example, and the upper and lower points (one of which is the $0^{th}$ point and the other of which is the 2th point) have potentials $V_0$ and $V_2$, respectively. The amounts of the electron and ion incident on the first point are represented by a flux density, respectively. It is assumed that the electron flux is $\Gamma_e$ and the ion flux is $\Gamma_p$. Then, the charge density $\rho$ at the first point is calculated by the formula (21). $V_1$, $V_2$, and $V_0$ can be calculated based on the processing surface potential and the bottom potential as well as the sequence of the respective points and the material conductivities at the respective points for example.

[Formula 24]

$$\rho = e(\Gamma_p - \Gamma_e) - \frac{V_1 - V_0}{R} - \frac{V_1 - V_2}{R} \tag{24}$$

As described above, the actual measurement data of the surface potential and the bottom potential in the charge-up sensor 11B modeling the processing face can be used in consideration of the side wall resistance of the processing groove to calculate the charge distribution of the processing groove surface, thereby finding the behavior of the charged particles in the groove.

Figure 18:
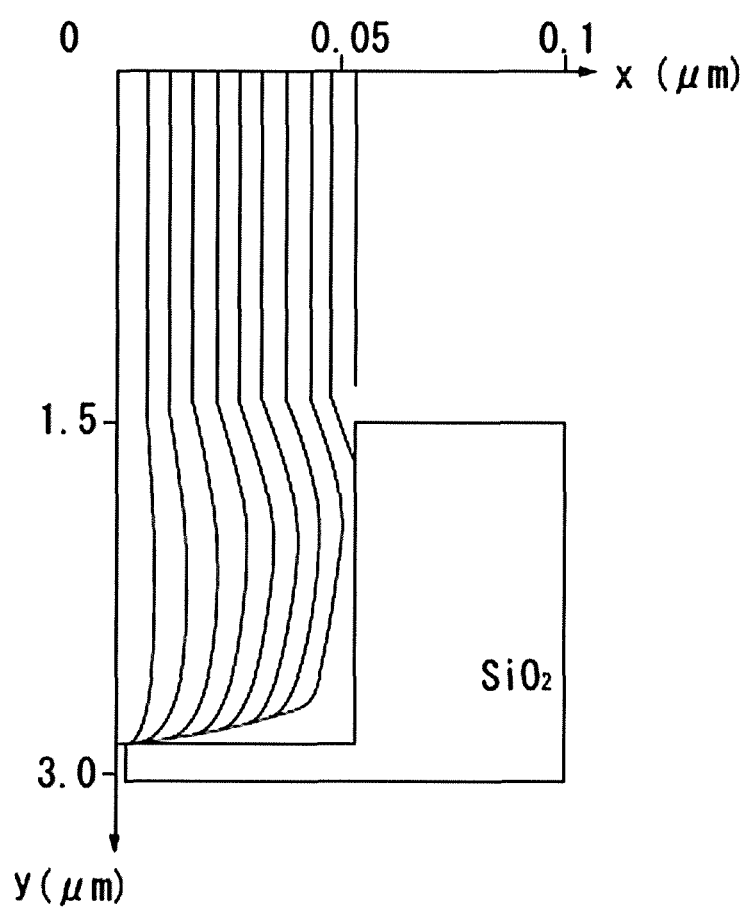
FIG. 18 is a view showing an ion trajectory calculated in the embodiment.

FIG. 18 illustrates the ion trajectory calculated in the embodiment. Conditions under which plasma is generated are set to Ar of 5 mT, the inductive coupling-type plasma power of 1 kW, and the substrate bias of 100 W. As can be seen from FIG. 18, it is expected that, as the ion trajectory is deeper, the ion trajectory is more concentrated on the center and thus the etching is tapered.

An etching object is the hole in the silicon oxide film but also may be a groove pattern or an electrode pattern. Material to be etched also may be a silicon nitride film, a silicon carbonitride film, or a carbon doped silicon oxide film.

Figure 19:
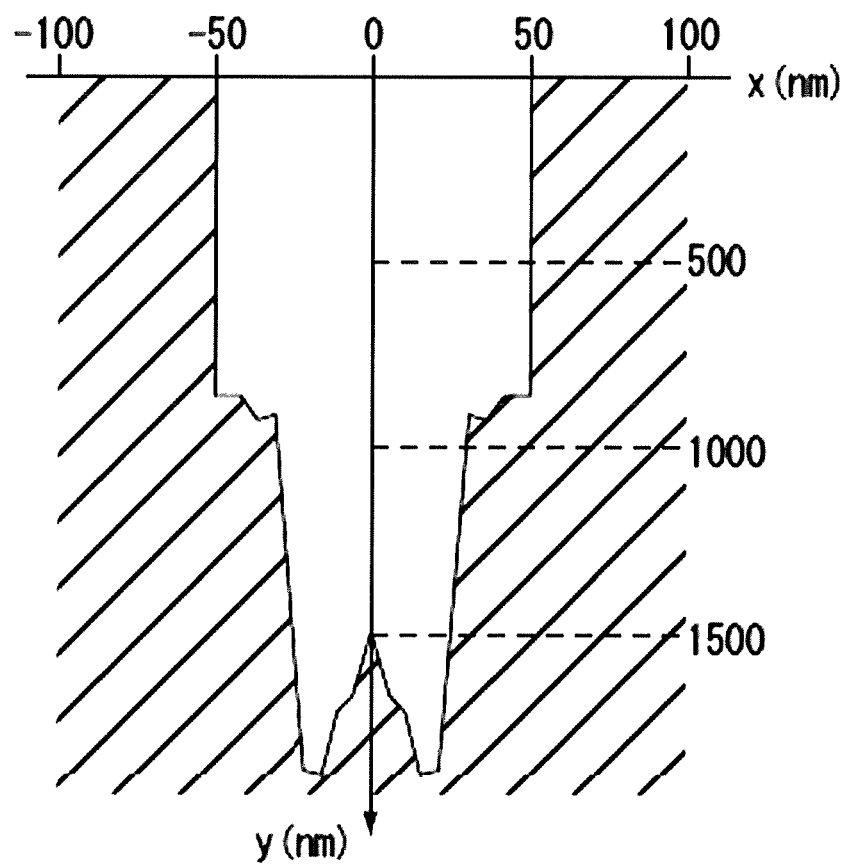
FIG. 19 is a view showing an etching shape calculated in the embodiment.

As described above, not only the ion trajectory but also the ion flux and energy were calculated simultaneously and the etching shape was calculated. FIG. 19 illustrates the calculated etching shape. As can be seen from FIG. 19, as the hole is deeper, the ion trajectory is concentrated on the hole center, thus providing a tapered etching shape.

In the embodiment of the present invention, not only the electrical measurement by the on-wafer monitoring sensor but also the information near the substrate are used to calculate the types of radicals or ions using the light emission spectroscopy or the mass analysis. Then, based on the calculated information, the etching shape can be calculated. For example, during the measurement by the on-wafer monitoring sensor, plasma light emission is measured through a view port of the chamber. Then, based on the light emission data, the types of radicals and flux flowing into the substrate can be calculated. By calculating in advance the relation between the data for these radicals and ions, the ion flux energy, and the processing amount of the to-be-etched material, the etching amount can be calculated.

REFERENCE SIGNS LIST

1: Plasma process processing shape prediction system
2: Network
10: Plasma processing apparatus
11: On-wafer monitoring sensor
11A: Sensor for sheath monitoring
11B: Charge-up sensor
11C: Ultra-violet sensor
12: Measurement
15: Chamber
20: Simulator
21: Apparatus condition DB
22: Incident ion DB
23: Incident radical DB
24: Actual measurement DB
25: Material property and surface reaction DB
26: Trajectory calculation unit
27: Surface shape calculation unit
28: GUI (Graphical User Interface)
30a: Filter
30b: DC power supply
30c: Measurement
31: Silicon substrate
32: Silicon oxide film
33: Al electrode (aluminum electrode)
34: Alumina film
35: Silicon substrate
36: Silicon oxide film
37: First polycrystalline silicon film
38: Silicon oxide film
39: Second polycrystalline silicon film
41: Silicon substrate
42: Silicon oxide film
43a and 43b: Polycrystalline silicon film
43: Polycrystalline silicon film
44: Insulator

What is claimed is:

1. A plasma processing system, comprising:
a plasma processing apparatus including a chamber in which a plasma process is applied to a semiconductor wafer, and an on-wafer sensor located in the chamber with the semiconductor wafer being processed by the plasma process, the on-wafer sensor measuring and outputting actual measurement data for monitoring a plasma state in the plasma process; and
a simulator connected to the plasma processing apparatus through a network and outputting a predicted surface shape for the semiconductor wafer to the plasma processing apparatus, the plasma processing apparatus changing a plasma processing condition to obtain a predetermined processing shape for the semiconductor wafer when the predicted surface shape varies from the predetermined processing shape,
wherein the simulator includes:
an incident ion database for storing, with regard to the respective operating conditions of the plasma processing apparatus, data regarding an incident energy distribution and an angle distribution of the flux of charged particles;
an incident radical database for storing, with regard to the respective operating conditions of the plasma processing apparatus, data regarding an incident energy distribution and an incident angle distribution of radicals;
a material property and surface reaction database for storing the respective coefficients for the respective reactions required for a radical adsorption reaction calculation, an ion reaction calculation and a thermal excitation-type chemical reaction calculation, respectively, and the property values of the respective materials required for a trajectory calculation and a reaction calculation;
an actual measurement database for storing, with regard to the respective operating conditions of the plasma processing apparatus, an electron temperature and an electron density from the actual measurement data outputted from the sensor so that the electron temperature and the electron density are associated with the data stored in the incident ion database and the incident radical database, respectively;
a trajectory calculation unit for calculating the trajectories of charged particles incident on the processing surface from plasma based on an electron temperature, an electron density, and an electron energy distribution calculated from a current-voltage characteristic from among the actual measurement data inputted from the sensor as well as a charge distribution at the processing surface or based on an ion current and sheath voltage calculated from the current-voltage characteristic and the charge distribution at the processing surface by calculating an electric field distribution from a Poisson equation based on the charge accumulation amount at the respective points of the processing surface as a boundary condition to repeatedly perform a trajectory calculation until the trajectories of charged particles subsequently flowing into the processing surface are convergent by the electric field distribution; and
a surface shape calculation unit for calculating the respective ions incident on the respective points of the processing surface based on the trajectories of the charged particles calculated by the trajectory calculation unit to use the data stored in the incident ion database, the incident radical database, the material property and surface reaction database, and the actual measurement database, for calculating the reactions at the respective points of the processing surface to calculate an etching rate and a deposition rate, and for calculating, based on a difference between the etching rate and the deposition rate, the transfer rates at the respective points of the processing surface to thereby calculate the predicted surface shape,
wherein the on-wafer sensor includes an ultra-violet sensor,
wherein the actual measurement database stores an ultra-violet absorption amount calculated based on the actual measurement data sent from the ultra-violet sensor, and
wherein the surface shape calculation unit calculates a defect generation distribution due to ultra-violet rays based on an ultra-violet absorption amount determined based on the actual measurement data sent from the ultra-violet sensor and the actual measurement database and an ultra-violet irradiation direction, selects the respective coefficients for the respective reactions stored in the material property and surface reaction database that are used for a radical adsorption reaction calculation, an ion reaction calculation, and a thermal excitation-type chemical reaction calculation based on the calculated defect generation distribution and the respective points on the processing surface, and calculates the etching rate and the deposition rate based on the reaction calculation in the respective points on the processing surface.

2. The processing system according to claim 1,
wherein the simulator further includes an apparatus condition database for storing information regarding an apparatus condition including the type of the plasma processing apparatus, a model number, and a processing condition, and
wherein the incident ion database, the incident radical database, and the actual measurement database are stored for the respective pieces of information stored in the apparatus condition database.

3. The processing system according to claim 1, wherein the on-wafer sensor in the chamber of the plasma processing apparatus includes a charge-up sensor having a groove, and
the trajectory calculation unit calculates charge densities at the respective points of a processing groove based on actual measurement data for a surface potential and a bottom potential of the groove sent from the charge-up sensor as well as a side wall resistance of the processing groove and a flux density of electrons and ions incident on the respective points of the processing groove to thereby calculate a charge distribution of the processing groove surface to subsequently calculate an electric field distribution.

4. A plasma processing method, comprising:
applying a plasma process having a plasma processing condition to a semiconductor wafer in a chamber of a plasma processing apparatus;
providing an on-wafer sensor in the chamber of the plasma processing apparatus with the semiconductor wafer being processed by the plasma process, the on-wafer sensor measuring and outputting actual measurement data to a simulator connected to the plasma processing through a network for monitoring a plasma state in the plasma process;

a trajectory calculation step performed by the simulator to calculate, based on an electron temperature, an electron density, and an electron energy distribution calculated from a current-voltage characteristic from among actual measurement data outputted by the sensor for plasma generated under a processing condition and a charge distribution at the processing surface or based on an ion current and a sheath voltage calculated from the current-voltage characteristic and the charge distribution at the processing surface, the trajectories of charged particles flowing from plasma into the processing surface by calculating an electric field distribution from a Poisson equation based on the charge accumulation amount at the respective points of the processing surface as a boundary condition to repeatedly perform a trajectory calculation until the trajectories of charged particles subsequently flowing into the processing surface are convergent by the electric field distribution;

a surface transfer rate calculation step performed by the simulator to calculate ion species incident on the respective points of the processing surface along the trajectories of the charged particles calculated in the trajectory calculation step and using an incident flux distribution of the ion species and radicals for calculating an etching rate and a deposition rate at the respective points of the processing surface to calculate, based on a difference between the etching rate and the deposition rate, the transfer rates at the respective points of the surface to thereby output a predicted surface shape from the simulator to the plasma processing apparatus;

changing the plasma processing condition of the plasma process to obtain a predetermined processing shape for the semiconductor wafer when the predicted surface shape received from the simulator varies from the predetermined processing shape; and a step performed by the simulator to determine, based on the transfer rates at the respective points of the processing surface calculated in the surface transfer rate calculation step, whether a processing amount set by the processing condition is satisfied or not to newly set, when the processing amount set by the processing condition is not satisfied, new points at the processing surface to return to the trajectory calculation step, wherein the surface transfer rate calculation step uses actual measurement data for an amount of ultra-violet rays incident on the respective points of the processing surface from plasma generated under the processing condition to calculate a defect distribution generated near the processing surface based on an ultra-violet absorption rate near the processing surface to reset, based on this defect distribution, adsorption rates and desorption rates of the respective radicals and ions to the processing surface for the respective points at the processing surface to thereby calculate the etching rates and the deposition rates at the respective points at the processing surface.

5. The plasma processing method according to claim 4, wherein the trajectory calculation step calculates charge densities at the respective points of a processing groove based on actual measurement data for a surface potential and a bottom potential from the charge-up sensor modeling the processing face as well as a side wall resistance of the processing groove and a flux density of electrons and ions incident on the respective points of the processing groove to thereby calculate a charge distribution of the processing groove surface to subsequently calculate an electric field distribution.

6. A non-transitory computer readable medium storing a program to be executed on a computer to control a plasma process applied to a semiconductor wafer in a plasma processing apparatus, the program comprising:

setting a plasma processing condition for the plasma process applied to the semiconductor wafer in a chamber of the plasma processing apparatus;

receiving actual measurement data for a plasma state in the plasma process measured and outputted from an on-wafer sensor located in the chamber of the plasma processing apparatus with the semiconductor wafer being processed by the plasma process, the on-wafer sensor measuring and outputting the actual measurement data;

a trajectory calculation step for calculating, based on an electron temperature, an electron density, and an electron energy distribution calculated from a current-voltage characteristic from among actual measurement data outputted by an on-wafer sensor for plasma generated under a processing condition and a charge distribution at the processing surface or based on an ion current and a sheath voltage calculated from the current-voltage characteristic and the charge distribution at the processing surface, the sensor being located in the plasma processing apparatus with a semiconductor wafer being processed by the plasma process, the on-wafer sensor measuring and outputting the actual measurement data for monitoring a plasma state in the plasma process, the trajectories of charged particles flowing from plasma into the processing surface by calculating an electric field distribution from a Poisson equation based on the charge accumulation amount at the respective points of the processing surface as a boundary condition to repeatedly perform a trajectory calculation until the trajectories of charged particles subsequently flowing into the processing surface are convergent by the electric field distribution;

a surface transfer rate calculation step for calculating ion species incident on the respective points of the processing surface along the trajectories of the charged particles calculated in the trajectory calculation step and using an incident flux distribution of the ion species and radicals for calculating an etching rate and a deposition rate at the respective points of the processing surface to calculate, based on a difference between the etching rate and the deposition rate, the transfer rates at the respective points of the surface to thereby output a predicted surface shape of the semiconductor wafer;

changing the plasma processing condition of the plasma processing apparatus to obtain a predetermined processing shape for the semiconductor wafer when the predicted surface shape varies from the predetermined processing shape; and a step for determining, based on the transfer rates at the respective points of the processing surface calculated in the surface transfer rate calculation step, whether a processing amount set by the processing condition is satisfied or not to newly set, when the processing amount set by the processing condition is not satisfied, new points at the processing surface to return to the trajectory calculation step, wherein the surface transfer rate calculation step uses actual measurement data for an amount of ultra-violet rays incident on the respective points of the processing surface from plasma generated under the processing condition to calculate a defect distribution generated near the processing surface based on an ultra-violet absorption rate near the processing surface to reset, based on this defect distribution, adsorption rates and desorption rates of the respective radicals and ions to the processing surface for the respective points at the processing surface to thereby calculate the etching rates and the deposition rates at the respective points at the processing surface.

7. The non-transitory computer readable medium according to claim 6, wherein the trajectory calculation step calculates charge densities at the respective points of a processing groove based on actual measurement data for a surface potential and a bottom potential from the charge-up sensor modeling the processing face as well as a side wall resistance of the processing groove and a flux density of electrons and ions incident on the respective points of the processing groove to thereby calculate a charge distribution of the processing groove surface to subsequently calculate an electric field distribution.

* * * * *